(12) United States Patent
Krusell et al.

(10) Patent No.: US 10,384,013 B2
(45) Date of Patent: Aug. 20, 2019

(54) PEN-TYPE DRUG INJECTOR AND ADD-ON MODULE WITH MAGNETIC DOSAGE SENSOR SYSTEM AND ERROR DETECTION

(71) Applicant: Novo Nordisk A/S, Bagsvaerd (DK)

(72) Inventors: Nikolaj Frogner Krusell, Copenhagen (DK); Preben Mikael Nielsen, Holbaek (DK); Jens Christian Andersen, Roskilde (DK)

(73) Assignee: Novo Nordisk A/S, Bagsvaerd (DK)

( * ) Notice: Subject to any disclaimer, the term of this patent is extended or adjusted under 35 U.S.C. 154(b) by 117 days.

(21) Appl. No.: 15/515,188

(22) PCT Filed: Oct. 1, 2015

(86) PCT No.: PCT/EP2015/072673
§ 371 (c)(1),
(2) Date: Mar. 29, 2017

(87) PCT Pub. No.: WO2016/050902
PCT Pub. Date: Apr. 7, 2016

(65) Prior Publication Data
US 2017/0232203 A1    Aug. 17, 2017

(30) Foreign Application Priority Data

Oct. 3, 2014    (EP) ..................................... 14187599
Nov. 24, 2014    (EP) ..................................... 14194548

(51) Int. Cl.
| | | |
|---|---|---|
| *A61M 5/315* | (2006.01) | |
| *A61M 5/20* | (2006.01) | |
| *A61M 5/24* | (2006.01) | |
| *A61M 5/28* | (2006.01) | |
| *A61M 5/31* | (2006.01) | |

(52) U.S. Cl.
CPC .......... *A61M 5/31553* (2013.01); *A61M 5/20* (2013.01); *A61M 5/24* (2013.01);
(Continued)

(58) Field of Classification Search
CPC .......... A61M 5/31568; A61M 5/31583; A61M 2205/3317; A61M 2205/3365; A61M 5/31553
See application file for complete search history.

(56) References Cited

U.S. PATENT DOCUMENTS 6,482,185 B1    11/2002    Hartmann
6,556,005 B1    4/2003    Oomkes
(Continued)

FOREIGN PATENT DOCUMENTS

WO    2003005891 A1    1/2003
WO    2007107564 A1    9/2007
(Continued)

*Primary Examiner* — Bradley J Osinski
(74) *Attorney, Agent, or Firm* — Wesley Nicolas

(57) ABSTRACT

Add-on module (100) for logging the value of an expelled dose from a pen-type drug injector (200), comprising a magnetic sensor system comprising first and second sensor means (745/746) as well as a mechanical dose setting and expelling mechanism comprising a magnetic clutch element (240/740) which rotates during drug expelling. The system further comprises processor means configured to determine (i) on the basis of measured values from the first sensor means, a rotational position of the clutch element, (ii) on the basis of measured values from the second sensor means, a high-speed condition in which the rotational speed of the clutch element exceeds a given threshold level, and (iii) indicate an error state if the high-speed condition is detected.

15 Claims, 10 Drawing Sheets

(52) U.S. Cl.
CPC ........ *A61M 5/288* (2013.01); *A61M 5/31511* (2013.01); *A61M 5/31525* (2013.01); *A61M 5/31541* (2013.01); *A61M 5/31568* (2013.01); *A61M 5/31583* (2013.01); *A61M 5/31595* (2013.01); *A61M 5/31593* (2013.01); *A61M 2005/3126* (2013.01); *A61M 2202/04* (2013.01); *A61M 2205/0227* (2013.01); *A61M 2205/18* (2013.01); *A61M 2205/3317* (2013.01); *A61M 2205/3365* (2013.01); *A61M 2205/502* (2013.01); *A61M 2205/52* (2013.01)

(56) References Cited

U.S. PATENT DOCUMENTS

| | | |
|---|---|---|
| 8,008,908 B2 | 8/2011 | Doogue et al. |
| 2009/0318865 A1 | 12/2009 | Moller et al. |
| 2014/0296782 A1* | 10/2014 | Ulrich .................. A61M 5/158 604/111 |
| 2016/0051764 A1* | 2/2016 | Dreier ................. A61M 5/3155 604/211 |

FOREIGN PATENT DOCUMENTS

| | | |
|---|---|---|
| WO | 2010037828 A1 | 4/2010 |
| WO | 2010052275 A2 | 5/2010 |
| WO | 2011117212 A1 | 9/2011 |
| WO | 2013050535 A2 | 4/2013 |
| WO | 2013063205 A1 | 5/2013 |
| WO | 2014108494 A1 | 7/2014 |
| WO | 2014111339 A1 | 7/2014 |
| WO | 2014161952 A1 | 10/2014 |

\* cited by examiner

— Actual value
— Estimated (Position algorithm [3 Hz])
— Estimated (Position algorithm [20 Hz])

PEN-TYPE DRUG INJECTOR AND ADD-ON MODULE WITH MAGNETIC DOSAGE SENSOR SYSTEM AND ERROR DETECTION

CROSS-REFERENCE TO RELATED APPLICATIONS

This application is a 35 U.S.C. § 371 National Stage application of International Application PCT/EP2015/072673 (published as WO 2016/050902), filed Oct. 1, 2015, which claims priority to European Patent Applications 14187599.7, filed Oct. 3, 2014 and 14194548.5, filed Nov. 24, 2014; the contents thereof which are incorporated by reference in their entirety.

The present invention generally relates to sensor systems adapted to detect rotational movement in a reliable and energy effective way. In a specific implementation the present invention relates to medical devices for which the generation, collecting and storing of data are relevant. In a specific aspect, the invention addresses the issue of reliably detecting movement of a member indicative of the operation of a drug delivery expelling mechanism.

BACKGROUND OF THE INVENTION

In the disclosure of the present invention reference is mostly made to drug delivery devices, such devices being used e.g. in the treatment of diabetes, however, this is only an exemplary use of the present invention.

Drug injection devices have greatly improved the lives of patients who must self-administer drugs and biological agents. Drug injection devices may take many forms, including simple disposable devices that are little more than an ampoule with an injection means or they may be durable devices adapted to be used with pre-filled cartridges. Regardless of their form and type, they have proven to be great aids in assisting patients to self-administer injectable drugs and biological agents. They also greatly assist care givers in administering injectable medicines to those incapable of performing self-injections.

Performing the necessary drug injection at the right time and in the right size is essential for managing diabetes, i.e. compliance with the specified drug regimen is important. In order to make it possible for medical personnel to determine the effectiveness of a prescribed dosage pattern, diabetes patients are encouraged to keep a log of the size and time of each injection. However, such logs are normally kept in handwritten notebooks, from the logged information may not be easily uploaded to a computer for data processing. Furthermore, as only events, which are noted by the patient, are logged, the note book system requires that the patient remembers to log each injection, if the logged information is to have any value in the treatment of the patient's disease. A missing or erroneous record in the log results in a misleading picture of the injection history and thus a misleading basis for the medical personnel's decision making with respect to future medication. Accordingly, it may be desirable to automate the logging of ejection information from medication delivery systems.

Though some injection devices integrate this monitoring/acquisition mechanism into the device itself, e.g. as disclosed in US 2009/0318865 and WO 2010/052275, most devices of today are without it. The most widely used devices are purely mechanical devices either durable or prefilled. The latter devices are to be discarded after being emptied and so inexpensive that it is not cost-effective to build-in electronic data acquisition functionality in the device it-self. Addressing this problem a number of solutions have been proposed which would help a user to generate, collect and distribute data indicative of the use of a given medical device.

For example, WO 2007/107564 describes an electronic "add-on" module adapted to be attached to and measure signals generated by a mechanical pen device. The detected signals may be used to detect different events, e.g. different sounds indicating setting a dose respectively ejecting a dose. A memory stores detected doses together with a time stamp, e.g. for several months. The module is provided with wireless means for transmitting detected data to an external unit, e.g. computer or another portable device (e.g. smartphone, PDA) for further processing and visualization. WO 2010/037828 discloses an arrangement for mounting such a module on a pen-formed drug delivery device. WO 2014/161952 and WO 2013/050535 disclose add-on modules adapted to be attached to and measure signals generated by a magnet incorporated in a mechanical pen device. Further external devices for a pen device are shown in U.S. Pat. No. 6,482,185, and WO 03/005891. WO 2011/117212 discloses a drug delivery system in which an add-on module is inserted into a cavity of a receiving device. In order to "wake-up" the electronic capturing means the add-on module may be provided with a mechanical cap-operated switch as disclosed e.g. in WO 2014/161952. Alternatively wake-up may be provided by electronic sensor means adapted to detect motion as disclosed e.g. in WO 2011/117212 and WO 2014/111339. The above-cited references are hereby incorporated by reference.

Having regard to the above, it is an object of the present invention to provide components, devices and methods allowing reliable and cost-effective detection of rotational movements. It is a further object to provide such components, devices and methods to be used to detect movements generated by a drug delivery expelling mechanism in order to determine amounts of expelled drug.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a first aspect of the invention a drug delivery system is provided, comprising a drug-filled cartridge or means for receiving a drug-filled cartridge, the cartridge comprising an outlet and an axially displaceable piston, first sensor means comprising one or more sensors each adapted to measure a magnetic field corresponding to at least two axes, second sensor means comprising one or more sensors each adapted to measure a magnetic field corresponding to at least one axis, and an expelling assembly for expelling an amount of drug from a reservoir. The expelling assembly comprises setting means allowing a user to set a dose amount of drug to be expelled, actuation means for releasing or driving the drug expelling assembly to expel the set dose amount, and an indicator element adapted to rotate during expelling of an amount of drug. The indicator element comprises a magnet moving together therewith, the magnet being configured to generate a spatial magnetic field which relative to the sensors varies corresponding to the spatial orientation of the magnet and thus the indicator element, thereby generating a spatial magnetic field which varies relative to each sensor as the indicator element moves. The system further comprises processor means configured to: on the basis of measured values from the first sensor means, determine a rotational position of the indicator element, calculate an expelled dose amount based on determined rotational positions of the first indicator means, on the basis of measured values from the second sensor means, determine a high-speed condition in which the rotational speed of the indicator element exceeds a given threshold level, and indicate an error state if the high-speed condition is detected.

By this arrangement a drug delivery system is provided comprising a sensor system adapted to detect error states which may occur only rarely, this allowing the dedicated rotary sensor system to be optimized for normal operational conditions and thus lover power consumption, this in contrast to e.g. WO 2013/063205 and U.S. Pat. No. 6,556,005 in which error checks are performed during normal operation of the sensor system.

The drug delivery system may further comprise third sensor means comprising one or more sensors each adapted to measure a magnetic field corresponding to at least one axis, wherein the processor means is configured to determine on the basis of measured values from the third sensor means the number of full rotations of the indicator element. Such an arrangement is useful in case the indicator may rotate more than 360 degrees.

In an exemplary embodiment the drug delivery system comprises a first sensor assembly comprising one or more sensors adapted to measure a magnetic field corresponding to a plurality of axes, wherein the first sensor means is provided by the sensor assembly operated to measure a magnetic field corresponding to a first number of axes, and the third sensor means is provided by the sensor assembly operated to measure a magnetic field corresponding to a second lower number of axes. The sensor(s) of the first sensor means may have a first sampling frequency, and the sensor(s) of the third sensor means may have a second higher sampling frequency.

The second sensor means may be provided by a second sensor assembly comprising one or more further sensors which may be adapted to detect a magnetic change-of-state, e.g. may be of the MGR type.

In exemplary embodiments the indicator element rotates during expelling of drug, and the processor means and sensor means form part of an electronically controlled capturing system for capturing data representing a property related to the amount of drug expelled from a reservoir by the expelling assembly during expelling of a set dose, the property being rotational movement of the indicator element.

The indicator element may be formed fully or partly of a polymeric material containing magnetic particles, the polymeric material having been magnetized to provide a magnet producing the magnetic spatial field, and wherein the indicator element may be ring-formed.

The above-described drug delivery systems may be in the form of an assembly comprising a drug delivery device and a logging device adapted to be releasably attached to a drug delivery device, wherein the drug delivery device comprises the expelling assembly, and the logging device comprises the first sensor means, the second sensor means, and the processor means.

In a second aspect of the invention a logging device adapted to be releasably attached to a drug delivery device is provided, the drug delivery device comprising a drug reservoir or means for receiving a drug reservoir, drug expelling means comprising dose setting means allowing a user to set a dose amount of drug to be expelled, and an indicator element comprising a magnet moving together therewith, the magnet being configured to generate a spatial magnetic field which relative to external sensor means varies corresponding to the rotational orientation of the magnet and thus the indicator element, wherein the indicator element is adapted to rotate during operation of the expelling means corresponding to an axis of rotation, the amount of rotation corresponding to the amount of drug expelled from a reservoir by the expelling means. The logging device comprises first sensor means comprising one or more sensors each adapted to measure a magnetic field corresponding to at least two axes, second sensor means comprising one or more sensors each adapted to measure a magnetic field corresponding to at least one axis, storage means adapted to store one or more dose amounts to create a log, and processor means configured to determine (i) on the basis of measured values from the first sensor means, a rotational position of the indicator element, (ii) on the basis of measured values from the second sensor means, a high-speed condition in which the rotational speed of the indicator element exceeds a given threshold level, and (iii) indicate an error state if the high-speed condition is detected.

The logging device may further comprise third sensor means comprising one or more sensors each adapted to measure a magnetic field corresponding to at least one axis, wherein the processor means is configured to determine on the basis of measured values from the third sensor means the number of full rotations of the indicator element.

The logging device may comprise a first sensor assembly comprising one or more sensors adapted to measure a magnetic field corresponding to a plurality of axes, wherein the first sensor means is provided by the sensor assembly operated to measure a magnetic field corresponding to a first number of axes, and the third sensor means is provided by the sensor assembly operated to measure a magnetic field corresponding to a second lower number of axes. The sensor(s) of the first sensor means may have a first sampling frequency, and the sensor(s) of the third sensor means may have a second higher sampling frequency.

In an exemplary embodiment the second sensor means is provided by a second sensor assembly comprising one or more further sensors which may be adapted to detect a magnetic change-of-state, e.g. may be of the MGR type.

In a further aspect of the invention a sensor system is provided comprising first sensor means comprising one or more sensors each adapted to measure a magnetic field corresponding to at least two axes, and second sensor means comprising one or more sensors each adapted to measure a magnetic field corresponding to at least one axis. The system comprises a mechanical assembly comprising an indicator element comprising a magnet moving together therewith, the magnet being configured to generate a spatial magnetic field which relative to the sensors varies corresponding to the spatial orientation of the magnet and thus the indicator element, thereby generating a spatial magnetic field which varies relative to each sensor as the indicator element moves, wherein the indicator element is adapted to rotate during operation of the assembly. The system further comprises processor means configured to determine (i) on the basis of measured values from the first sensor means, a rotational position of the indicator element, (ii) on the basis of measured values from the second sensor means, a high-speed condition in which the rotational speed of the indicator element exceeds a given threshold level, and (iii) indicate an error state if the high-speed condition is detected.

By this arrangement a rotary sensor system is provided comprising a sensor system adapted to detect error conditions which may occur only rarely, this allowing the dedicated rotary sensor system to be optimized for normal operational conditions and thus lover power consumption.

The first sensor means may be provided by a first sensor assembly comprising one or more sensors adapted to measure a magnetic field corresponding to a plurality of axes, and the second sensor means may be provided by a second sensor assembly comprising one or more further sensors. The latter may be adapted to detect a magnetic change-of-state, e.g. may be of the MGR type. Alternatively the system may comprise a sensor assembly comprising one or more sensors adapted to measure a magnetic field corresponding to a plurality of axes, wherein the first sensor means is provided by the sensor assembly operated to measure a magnetic field corresponding to a first number of axes, and the second sensor means is provided by the sensor assembly operated to measure a magnetic field corresponding to a second lower number of axes.

In exemplary embodiments the system further comprises third sensor means comprising one or more sensors each adapted to measure a magnetic field corresponding to at least one axis, wherein the processor means is configured to determine on the basis of measured values from the third sensor means the number of full rotations of the indicator element. The system may comprise a sensor assembly having one or more sensors adapted to measure a magnetic field corresponding to a plurality of axes, wherein the first sensor means is provided by the sensor assembly operated to measure a magnetic field corresponding to a first number of axes, and the third sensor means is provided by the sensor assembly operated to measure a magnetic field corresponding to a second lower number of axes. The sensor(s) of the first sensor means may be operated at a first sampling frequency, and the sensor(s) of the third sensor means may be operated at a second higher sampling frequency.

The indicator element may be formed fully or partly of a polymeric material containing magnetic particles, the polymeric material having been magnetized to provide a magnet producing the magnetic spatial field.

In the different aspect of the invention the "indicator element comprising a magnet moving together therewith" may be provided as a unitary element forming the magnet per se. The indicator element may have any suitable design for a given mechanical assembly, e.g. ring-formed.

As described above, the drug delivery system may be in the form of an assembly comprising a drug delivery device comprising a drug reservoir or means for receiving a drug reservoir, the expelling means, and a logging device (module) releasably attachable to the drug delivery device and comprising electronic circuitry adapted to create a log of expelled dose amounts of drug, the logging module comprising the sensor assembly adapted to capture a property value related to a dose amount of drug expelled from a reservoir by the expelling means during an expelling event, and the processor means adapted to determine dose amounts based on the captured property values. A cap is releasably attachable to the logging module to cover an outlet portion of a mounted drug reservoir.

To prevent that a given logging module is used in a way resulting in incorrect determination of dose data, the system comprises in exemplary embodiments means to ensure that a given logging module in a given state is used in combination with the corresponding drug, e.g. mechanical or electronic coding.

Correspondingly, the logging unit may be provided with an electronically controlled means for capturing information from an identifier on the drug delivery device, such that a log is created for a given identifier. The identifier may represent a given specific type of drug or a given unique drug delivery device. The identifier may be in the form of a colour marking, a barcode (e.g. 2D) or in the form of a pattern of conductive elements. The means for capturing information from the identifier may comprise a sensor adapted to capture information during movement of the sensor relative to the identifier.

Designing an electronic logging unit, that can automatically identify and recognise drug delivery devices with different contents will allow manufacturers a simpler and more cost efficient production and provide increased safety of the users.

In case mechanical coding is used, only mating codes may allow a give logging device to be mounted on a corresponding drug delivery device.

In the context of the present application and as used in the specification and the claims, the term processor means covers any combination of electronic circuitry suitable for providing the specified functionality, e.g. processing and storing data as well as controlling all connected input and output devices. A processor will typically comprise one or more CPUs or microprocessors which may be supplemented by additional devices for support, storage or control functions. For example, in case a communication interface is provided (e.g. wireless), the transmitter and receiver may be fully or partly integrated with a processor, or may be provided by individual units. Each of the components making up the processor circuitry may be special purpose or general purpose devices. The term display means covers any type of display capable of visually providing the specified functionality, e.g. a LCD or an OLED display.

As used herein, the term "insulin" is meant to encompass any drug-containing flowable medicine capable of being passed through a delivery means such as a cannula or hollow needle in a controlled manner, such as a liquid, solution, gel or fine suspension, and which has a blood glucose controlling effect, e.g. human insulin and analogues thereof as well as non-insulins such as GLP-1 and analogues thereof. In the description of exemplary embodiments reference will be made to the use of insulin.

BRIEF DESCRIPTION OF THE DRAWINGS

In the following embodiments of the invention will be described with reference to the drawings, wherein.

In the figures like structures are mainly identified by like reference numerals.

DESCRIPTION OF EXEMPLARY EMBODIMENTS

When in the following terms such as "upper" and "lower" or similar relative expressions are used, these only refer to the appended figures and not necessarily to an actual situation of use. The shown figures are schematic representations for which reason the configuration of the different structures as well as their relative dimensions are intended to serve illustrative purposes only. When the term member or element is used for a given component it generally indicates that in the described embodiment the component is a unitary component, however, the same member or element may alternatively comprise a number of sub-components just as two or more of the described components could be provided as unitary components, e.g. manufactured as a single injection moulded part. When it is defined that members are mounted axially free to each other it generally indicates that they can be moved relative to each other, typically between defined stop positions whereas when it is defined that members are mounted rotationally free to each other it generally indicates that they can be rotated relative to each other either freely or between defined stop positions. The terms "assembly" and "subassembly" do not imply that the described components necessary can be assembled to provide a unitary or functional assembly or subassembly during a given assembly procedure but is merely used to describe components grouped together as being functionally more closely related.

Figure 1A:
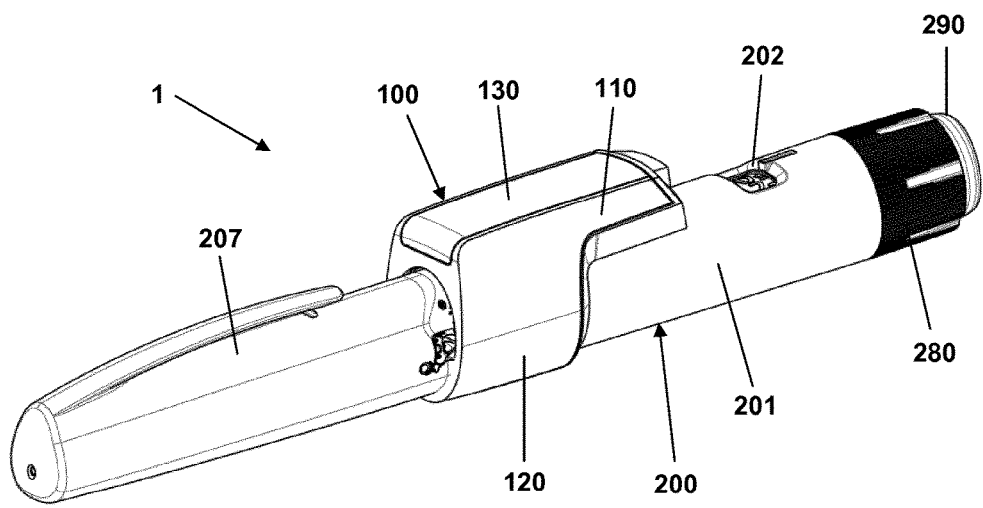
FIG. 1A shows a system comprising a logging module mounted on a pen device.
Figure 1B:
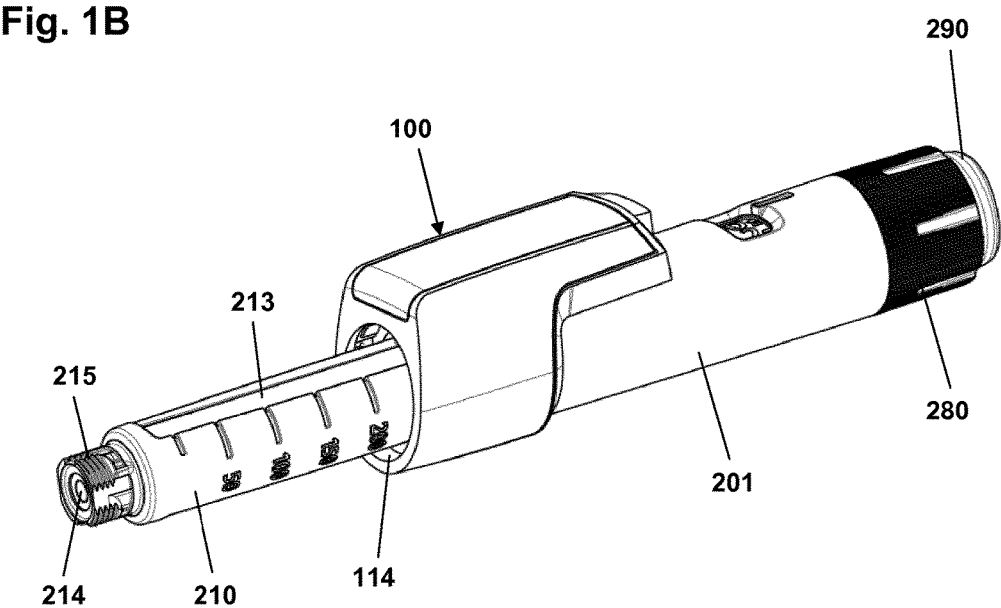
FIG. 1B shows the system of FIG. 1A with the pen cap removed.

FIGS. 1A and 1B show a drug delivery assembly 1 with a pen-formed drug delivery device 200 on which an electronic logging device (or module) 100 is mounted. In the present context the device represents a "generic" drug delivery device providing a specific example of a device in combination with which embodiments of the present invention is intended to be used or which can form a basis for aspects of the present invention.

More specifically, the logging module 100 comprises a body portion 110 and a ring-formed portion 120 allowing the module to be mounted on a generally cylindrical pen device. The body portion comprises electronic circuitry and sensor means allowing a property to be detected representing an amount of drug being expelled from the cartridge, as well as a display 130 for displaying data to a user. The ring portion comprises coupling means allowing the module to be securely and correctly mounted on the pen body. The electronic circuitry and the sensor means may in part be arranged in the ring portion. Exemplary embodiments of a logging module will be described with reference to FIGS. 6-10 below.

The pen device 200 comprises a cap part 207 and a main part having a proximal body or drive assembly portion with a housing 201 in which a drug expelling mechanism is arranged or integrated, and a distal cartridge holder portion in which a drug-filled transparent cartridge 213 with a distal needle-penetrable septum 214 is arranged and retained in place by a non-removable cartridge holder attached to the proximal portion, the cartridge holder having openings allowing a portion of the cartridge to be inspected as well as distal coupling means 215 allowing a needle assembly to be releasably mounted. The cartridge is provided with a piston driven by a piston rod forming part of the expelling mechanism and may for example contain an insulin, GLP-1 or growth hormone formulation. A proximal-most rotatable dose member 280 serves to manually set a desired dose of drug shown in display window 202 and which can then be expelled when the button 290 is actuated. Depending on the type of expelling mechanism embodied in the drug delivery device, the expelling mechanism may comprise a spring as in the shown embodiment which is strained during dose setting and then released to drive the piston rod when the release button is actuated. Alternatively a pre-tensioned spring for delivering the entire cartridge content in user settable doses may be used, see e.g. WO 2014/166887. As a further alternative the expelling mechanism may be fully manual in which case the dose member and the actuation button moves proximally during dose setting corresponding to the set dose size, and then is moved distally by the user to expel the set dose.

As appears, FIG. 1 shows a drug delivery device of the pre-filled type, i.e. it is supplied with a pre-mounted cartridge and is to be discarded when the cartridge has been emptied. In alternative embodiments the drug delivery device may be designed to allow a loaded cartridge to be replaced, e.g. in the form of a "rear-loaded" drug delivery device in which the cartridge holder is adapted to be removed from the device main portion, or alternatively in the form of a "front-loaded" device in which a cartridge is inserted through a distal opening in the cartridge holder which is non-removable attached to the main part of the device.

As the is module adapted to be secured to and interact with a drug delivery device, as well as a drug delivery device allowing such an interaction, an exemplary embodiment of such a device will be described for better understanding of the invention.

Figure 2:
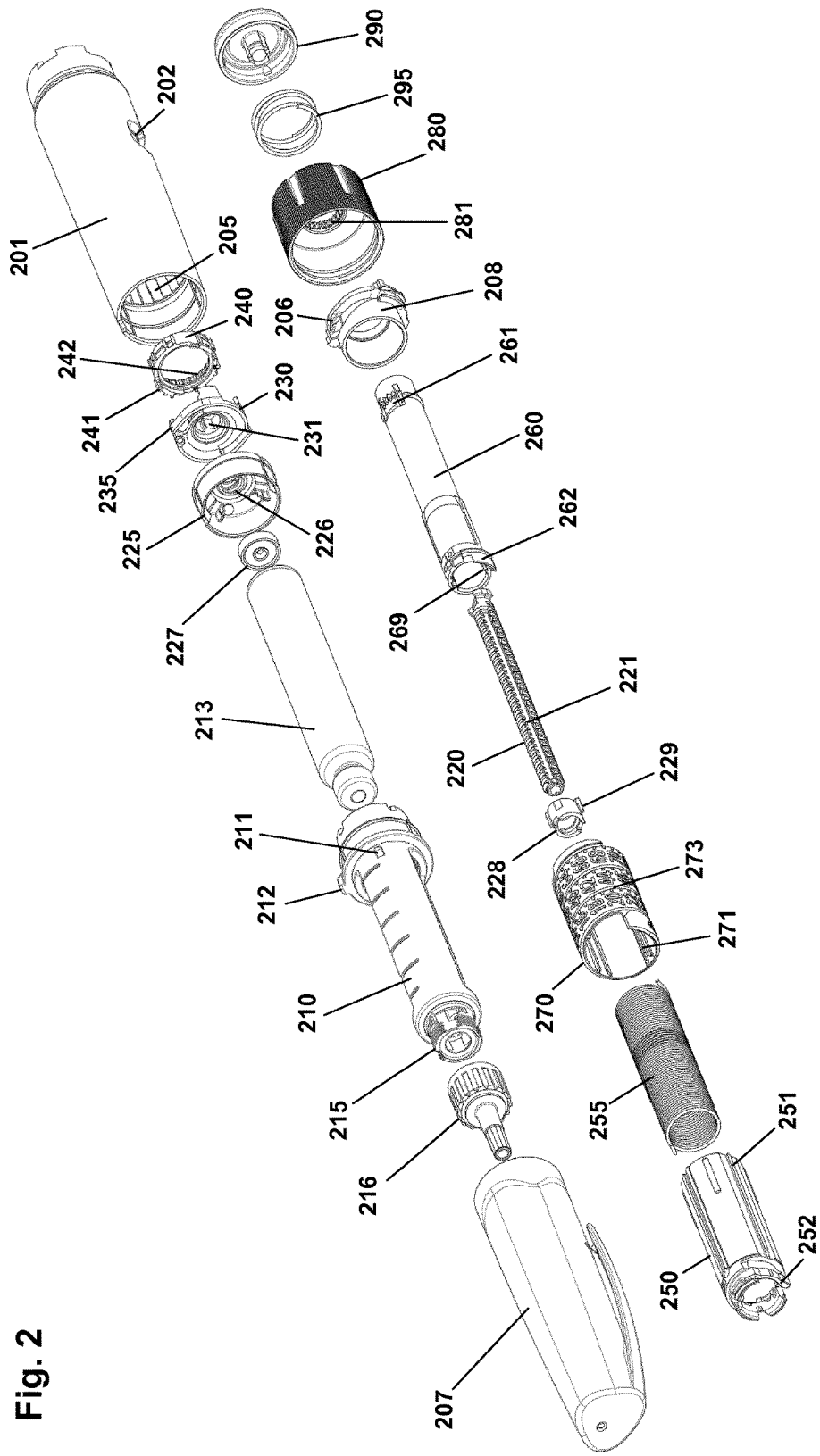
FIG. 2 shows in an exploded view the components of the pen device of FIG. 1A, FIGS. 3A and 3B show in sectional views an expelling mechanism in two states.

FIG. 2 shows an exploded view of the pen-formed drug delivery device 200 shown in FIG. 1. More specifically, the pen comprises a tubular housing 201 with a window opening 202 and onto which a cartridge holder 210 is fixedly mounted, a drug-filled cartridge 213 being arranged in the cartridge holder. The cartridge holder is provided with distal coupling means 215 allowing a needle assembly 216 to be releasably mounted, proximal coupling means in the form of two opposed protrusions 211 allowing a cap 207 to be releasably mounted covering the cartridge holder and a mounted needle assembly, as well as a protrusion 212 preventing the pen from rolling on e.g. a table top. In the housing distal end a nut element 225 is fixedly mounted, the nut element comprising a central threaded bore 226, and in the housing proximal end a spring base member 208 with a central opening is fixedly mounted. A drive system comprises a threaded piston rod 220 having two opposed longitudinal grooves and being received in the nut element threaded bore, a ring-formed piston rod drive element 230 rotationally arranged in the housing, and a ring-formed clutch element 240 which is in rotational engagement with the drive element (see below), the engagement allowing axial movement of the clutch element. The clutch element is provided with outer spline elements 241 adapted to engage corresponding splines 204 (see FIG. 4B) on the housing inner surface, this allowing the clutch element to be moved between a rotationally locked proximal position, in which the splines are in engagement, and a rotationally free distal position in which the splines are out of engagement. As just mentioned, in both positions the clutch element is rotationally locked to the drive element. The drive element comprises a central bore with two opposed protrusions 231 in engagement with the grooves on the piston rod whereby rotation of the drive element results in rotation and thereby distal axial movement of the piston rod due to the threaded engagement between the piston rod and the nut element. The drive element further comprises a pair of opposed circumferentially extending flexible ratchet arms 235 adapted to engage corresponding ratchet teeth 205 arranged on the housing inner surface. The drive element and the clutch element comprise cooperating coupling structures rotationally locking them together but allowing the clutch element to be moved axially, this allowing the clutch element to be moved axially to its distal position in which it is allowed to rotate, thereby transmitting rotational movement from the dial system (see below) to the drive system. The interaction between the clutch element, the drive element and the housing will be shown and described in greater detail with reference to FIGS. 4A and 4B.

On the piston rod an end-of-content (EOC) member 228 is threadedly mounted and on the distal end a washer 227 is rotationally mounted. The EOC member comprises a pair of opposed radial projections 229 for engagement with the reset tube (see below).

The dial system comprises a ratchet tube 250, a reset tube 260, a scale drum 270 with an outer helically arranged row of dose numerals, a user-operated dial member 280 for setting a dose of drug to be expelled, a release button 290 and a torque spring 255 (see FIG. 3). The reset tube is mounted axially locked inside the ratchet tube but is allowed to rotate a few degrees (see below). The reset tube comprises on its inner surface two opposed longitudinal grooves 269 adapted to engage the radial projections 229 of the EOC member, whereby the EOC can be rotated by the reset tube but is allowed to move axially. The clutch element is mounted axially locked on the outer distal end portion of the ratchet tube 250, this providing that the ratchet tube can be moved axially in and out of rotational engagement with the housing via the clutch element. The dial member 280 is mounted axially locked but rotationally free on the housing proximal end, the dial ring being under normal operation rotationally locked to the reset tube (see below), whereby rotation of dial ring results in a corresponding rotation of the reset tube and thereby the ratchet tube. The release button 290 is axially locked to the reset tube but is free to rotate. A return spring 295 provides a proximally directed force on the button and the thereto mounted reset tube. The scale drum 270 is arranged in the circumferential space between the ratchet tube and the housing, the drum being rotationally locked to the ratchet tube via cooperating longitudinal splines 251, 271 and being in rotational threaded engagement with the inner surface of the housing via cooperating thread structures 203, 273, whereby the row of numerals passes the window opening 203 in the housing when the drum is rotated relative to the housing by the ratchet tube. The torque spring is arranged in the circumferential space between the ratchet tube and the reset tube and is at its proximal end secured to the spring base member 208 and at its distal end to the ratchet tube, whereby the spring is strained when the ratchet tube is rotated relative to the housing by rotation of the dial member. A ratchet mechanism with a flexible ratchet arm 252 is provided between the ratchet tube and the clutch element, the latter being provided with an inner circumferential teeth structures 242, each tooth providing a ratchet stop such that the ratchet tube is held in the position to which it is rotated by a user via the reset tube when a dose is set. In order to allow a set dose to be reduced a ratchet release mechanism 262 is provided on the reset tube and acting on the ratchet tube, this allowing a set dose to be reduced by one or more ratchet increments by turning the dial member in the opposite direction, the release mechanism being actuated when the reset tube is rotated the above-described few degrees relative to the ratchet tube.

Figure 3A:
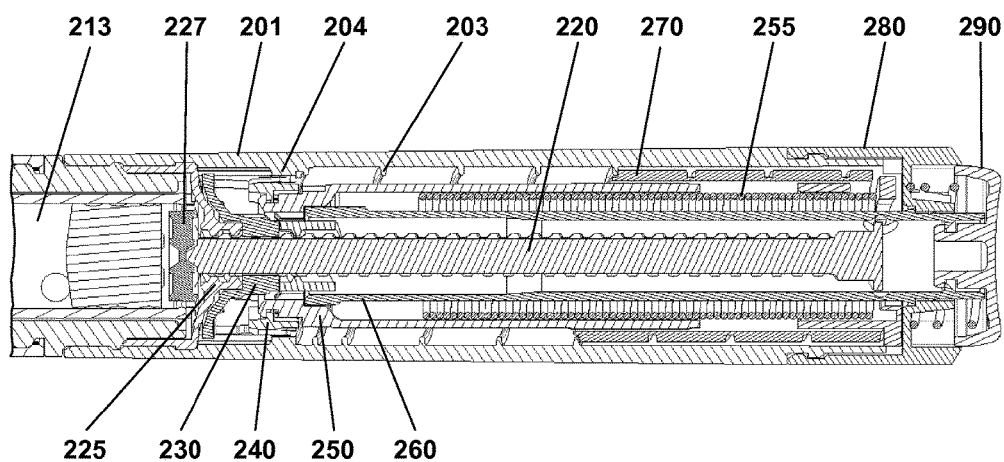

Having described the different components of the expelling mechanism and their functional relationship, operation of the mechanism will be described next with reference mainly to FIGS. 3A and 3B.

The pen mechanism can be considered as two interacting systems, a dose system and a dial system, this as described above. During dose setting the dial mechanism rotates and the torsion spring is loaded. The dose mechanism is locked to the housing and cannot move. When the push button is pushed down, the dose mechanism is released from the housing and due to the engagement to the dial system, the torsion spring will now rotate back the dial system to the starting point and rotate the dose system along with it.

The central part of the dose mechanism is the piston rod 220, the actual displacement of the plunger being performed by the piston rod. During dose delivery, the piston rod is rotated by the drive element 230 and due to the threaded interaction with the nut element 225 which is fixed to the housing, the piston rod moves forward in the distal direction. Between the rubber piston and the piston rod, the piston washer 227 is placed which serves as an axial bearing for the rotating piston rod and evens out the pressure on the rubber piston. As the piston rod has a non-circular cross section where the piston rod drive element engages with the piston rod, the drive element is locked rotationally to the piston rod, but free to move along the piston rod axis. Consequently, rotation of the drive element results in a linear forwards movement of the piston. The drive element is provided with small ratchet arms 234 which prevent the drive element from rotating clockwise (seen from the push button end). Due to the engagement with the drive element, the piston rod can thus only move forwards. During dose delivery, the drive element rotates anti-clockwise and the ratchet arms 235 provide the user with small clicks due to the engagement with the ratchet teeth 205, e.g. one click per unit of insulin expelled.

Turning to the dial system, the dose is set and reset by turning the dial member 280. When turning the dial, the reset tube 260, the EOC member 228, the ratchet tube 250 and the scale drum 270 all turn with it. As the ratchet tube is connected to the distal end of the torque spring 255, the spring is loaded. During dose setting, the arm 252 of the ratchet performs a dial click for each unit dialed due to the interaction with the inner teeth structure 242 of the clutch element. In the shown embodiment the clutch element is provided with 24 ratchet stops providing 24 clicks (increments) for a full 360 degrees rotation relative to the housing. The spring is preloaded during assembly which enables the mechanism to deliver both small and large doses within an acceptable speed interval. As the scale drum is rotationally engaged with the ratchet tube, but movable in the axial direction and the scale drum is in threaded engagement with the housing, the scale drum will move in a helical pattern when the dial system is turned, the number corresponding to the set dose being shown in the housing window 202.

The ratchet 252, 242 between the ratchet tube and the clutch element 240 prevents the spring from turning back the parts. During resetting, the reset tube moves the ratchet arm 252, thereby releasing the ratchet click by click, one click corresponding to one unit IU of insulin in the described embodiment. More specifically, when the dial member is turned clockwise, the reset tube simply rotates the ratchet tube allowing the arm of the ratchet to freely interact with the teeth structures 242 in the clutch element. When the dial member is turned counter-clockwise, the reset tube interacts directly with the ratchet click arm forcing the click arm towards the centre of the pen away from the teeth in the clutch, thus allowing the click arm on the ratchet to move "one click" backwards due to torque caused by the loaded spring.

Figure 3B:
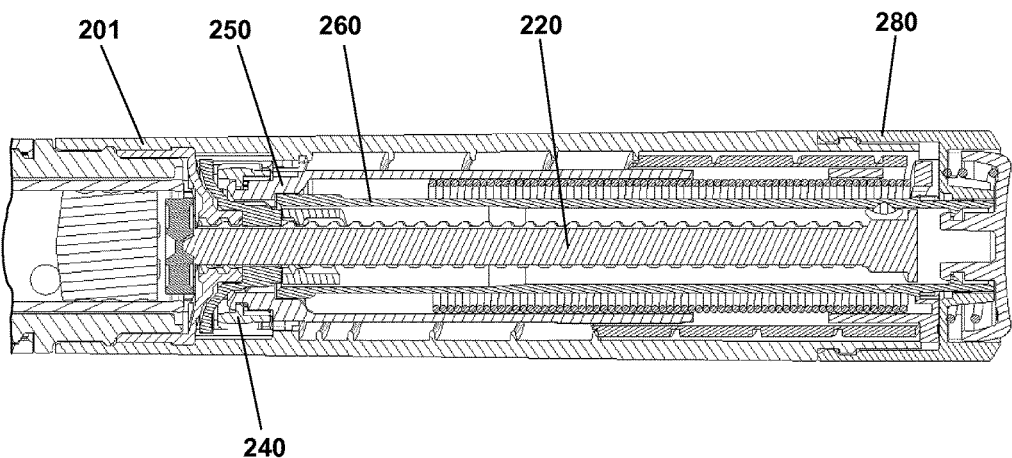

To deliver a set dose, the push button 290 is pushed in the distal direction by the user as shown in FIG. 3B. The reset tube 260 decouples from the dial member and subsequently the clutch element 240 disengages the housing splines 204. Now the dial mechanism returns to "zero" together with the drive element 230, this leading to a dose of drug being expelled. It is possible to stop and start a dose at any time by releasing or pushing the push button at any time during drug delivery. A dose of less than 5 IU normally cannot be paused, since the rubber piston is compressed very quickly leading to a compression of the rubber piston and subsequently delivery of insulin when the piston returns to the original dimensions.

The EOC feature prevents the user from setting a larger dose than left in the cartridge. The EOC member 228 is rotationally locked to the reset tube, which makes the EOC member rotate during dose setting, resetting and dose delivery, during which it can be moved axially back and forth following the thread of the piston rod. When it reaches the proximal end of the piston rod a stop is provided, this preventing all the connected parts, including the dial member, from being rotated further in the dose setting direction, i.e. the now set dose corresponds to the remaining drug content in the cartridge.

The scale drum 270 is provided with a distal stop surface adapted to engage a corresponding stop surface on the housing inner surface, this providing a maximum dose stop for the scale drum preventing all the connected parts, including the dial member, from being rotated further in the dose setting direction. In the shown embodiment the maximum dose is set to 80 IU. Correspondingly, the scale drum is provided with a proximal stop surface adapted to engage a corresponding stop surface on the spring base member, this preventing all the connected parts, including the dial member, from being rotated further in the dose expelling direction, thereby providing a "zero" stop for the entire expelling mechanism.

To prevent accidental over-dosage in case something should fail in the dialing mechanism allowing the scale drum to move beyond its zero-position, the EOC member serves to provide a security system. More specifically, in an initial state with a full cartridge the EOC member is positioned in a distal-most axial position in contact with the drive element. After a given dose has been expelled the EOC member will again be positioned in contact with the drive element. Correspondingly, the EOC member will lock against the drive element in case the mechanism tries to deliver a dose beyond the zero-position. Due to tolerances and flexibility of the different parts of the mechanism the EOC will travel a short distance allowing a small "over dose" of drug to be expelled, e.g. 3-5 IU of insulin.

The expelling mechanism further comprises an end-of-dose (EOD) click feature providing a distinct feedback at the end of an expelled dose informing the user that the full amount of drug has been expelled. More specifically, the EOD function is made by the interaction between the spring base and the scale drum. When the scale drum returns to zero, a small click arm 206 on the spring base is forced backwards by the progressing scale drum. Just before "zero" the arm is released and the arm hits a countersunk surface on the scale drum.

The shown mechanism is further provided with a torque limiter in order to protect the mechanism from overload applied by the user via the dial member. This feature is provided by the interface between the dial member and the reset tube which as described above are rotationally locked to each other. More specifically, the dial member is provided with a circumferential inner teeth structure 281 engaging a number of corresponding teeth arranged on a flexible carrier portion 261 of the reset tube. The reset tube teeth are designed to transmit a torque of a given specified maximum size, e.g. 150-300 Nmm, above which the flexible carrier portion and the teeth will bend inwards and make the dial member turn without rotating the rest of the dial mechanism. Thus, the mechanism inside the pen cannot be stressed at a higher load than the torque limiter transmits through the teeth.

Figure 4A:
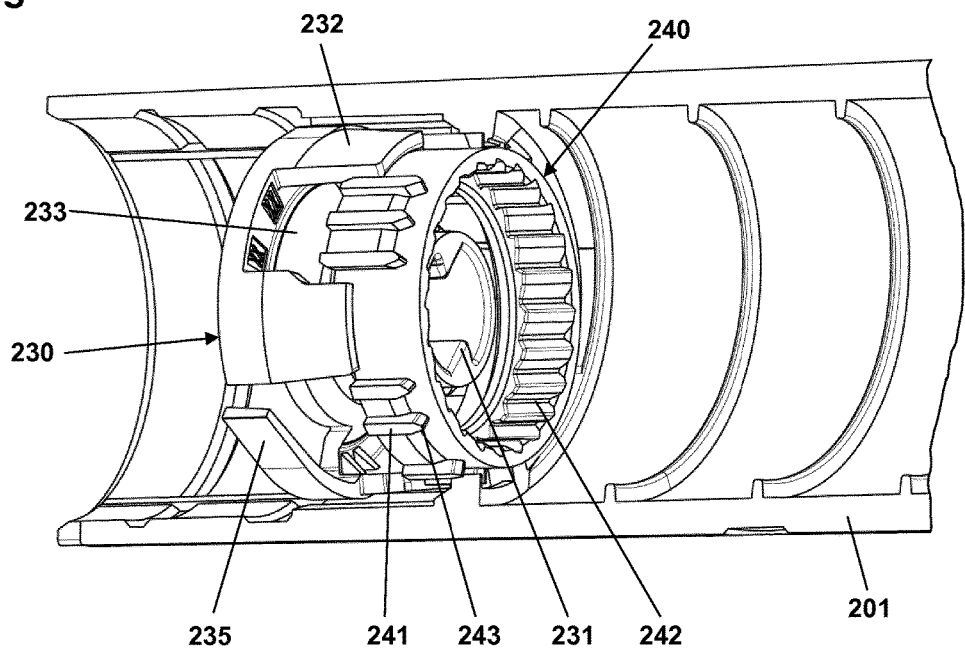
FIGS. 4A-4C show components of the pen device of FIG. 2.
Figure 4B:
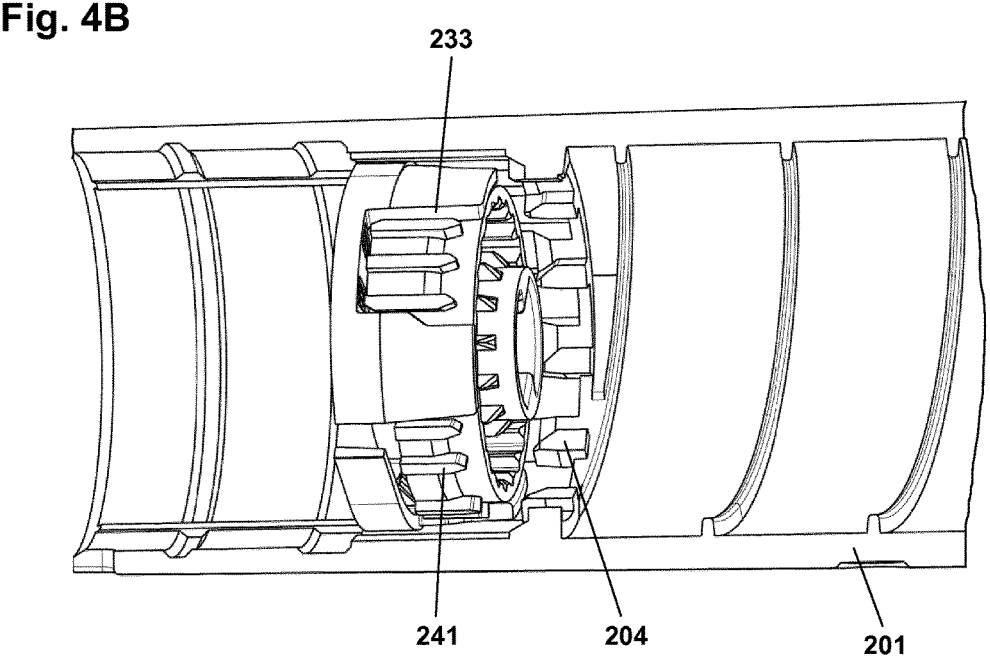
Figure 4C:
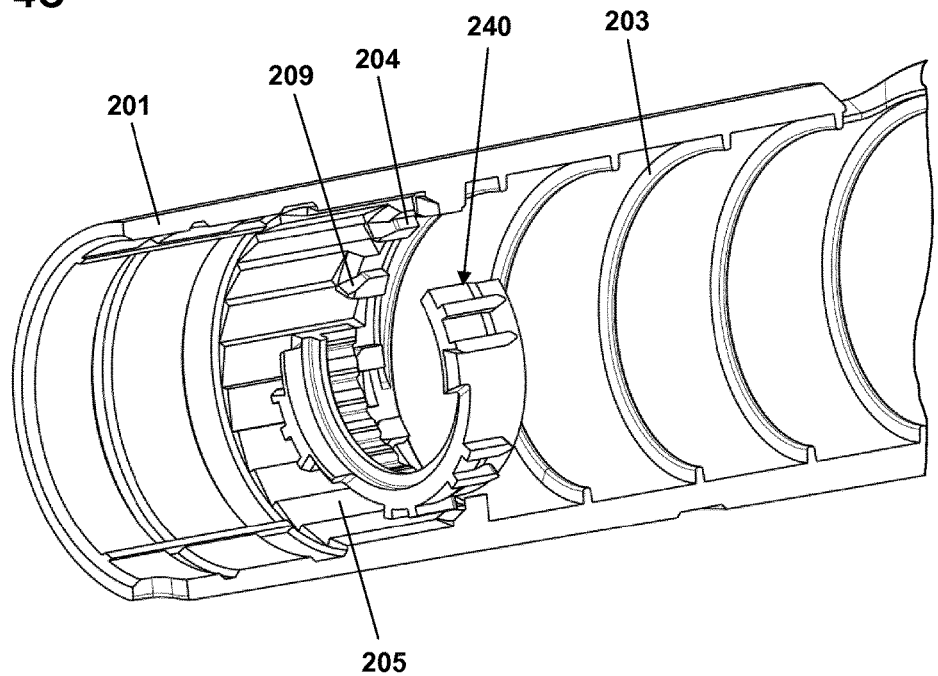

In FIG. 4A the clutch element, the drive element and the housing (in partial) are shown in the dose setting state, and in FIG. 4B the same components are shown in the expelling state. As appears, the piston rod on which the drive element is arranged and the ratchet tube on which the clutch element is mounted are not shown. To better show the structures provided on the inner surface of the housing FIG. 4C shows a partial clutch element 240 arranged in the housing 201.

The inner surface of the housing 201 comprises a circumferential ring-formed array of axially oriented spline elements 204 protruding into the interior, each having a pointed distal end 209, as well as a circumferential ring-formed array of one-way ratchet teeth 205. The inner surface further comprises a male helical thread 203 adapted to engage the female helical thread 273 on the scale drum 270. A distal circumferential groove is formed to engage and mount the nut element 225. The clutch element 240 comprises an inner circumferential ring-formed array of ratchet teeth 242 adapted to engage the ratchet arm 252 on the ratchet tube 250, and an outer circumferential ring-formed array of axially oriented spline elements 241 adapted to engage the spline elements 204 of the housing as well as the coupling slots in the drive element (see below), each spline having a pointed proximal end 243. The drive element 230 comprises a pair of opposed coupling portions each comprising two proximally extending skirt portions 232 between which an axially extending coupling slot 233 is formed, the slot being adapted to engage a portion of the clutch element spline elements. In this way the engaging surfaces serve to transmit a rotational force and thereby torque from the clutch element to the drive element in the expelling state. The drive element further comprises a pair of opposed circumferentially extending flexible ratchet arms adapted to engage the ring-formed array of one-way ratchet teeth 205. During dose delivery, the drive element rotates anti-clockwise and the ratchet arms 235 also provide the user with small clicks due to the engagement with the ratchet teeth 205, e.g. one click per unit of insulin expelled. In the shown embodiment 24 ratchet teeth are provided corresponding to 15 degrees rotation per unit of insulin. The central bore of the drive element comprises two opposed protrusions 231 adapted to engage with the axially oriented grooves on the piston rod.

In the dose setting state shown in FIG. 4A the spline elements 241 of the clutch element are in engagement with the spline elements 204 of the housing thereby rotationally locking the clutch element relative to the housing. As can be seen from FIG. 4A a group of clutch spline elements are received in the corresponding coupling slot with a slight rotational play. In the expelling state shown in FIG. 4B the spline elements 241 of the clutch element are moved distally out of engagement with the spline elements 204 of the housing thereby allowing rotation of the clutch element relative to the housing. As can be seen from FIG. 4B the group of clutch spline elements are now received in the corresponding coupling slot without rotational play.

When a dose has just been expelled movement of the clutch element has stopped but it is still in its distal position. Subsequently, when the user releases pressure on the release button the clutch element returns to its proximal position, however, due to the definite number of splines the clutch element will often rotate a small amount when doing so. Correspondingly, the expelling mechanism is not in a stable condition until the clutch element has returned to the initial proximal position.

Figure 5:
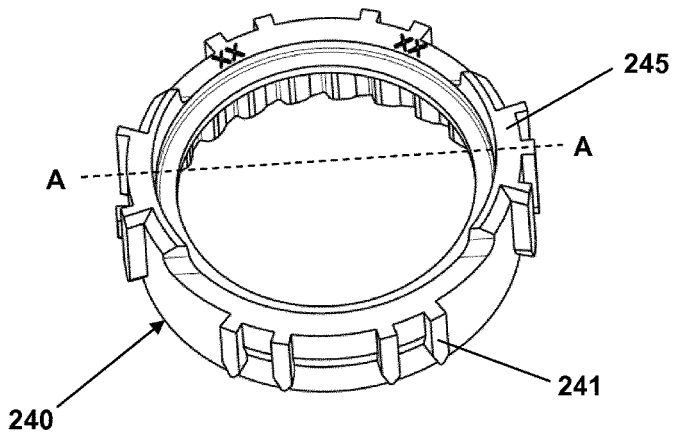
FIG. 5 shows a component of the pen device of FIG. 2.

FIG. 5 shows a detail view of the clutch element 240 showing the above-described inner circumferential ring-formed array of ratchet teeth 242 and the outer circumferential ring-formed array of axially oriented spline elements 241. As appears, the spline elements are not arranged equidistantly on the ring but in groups, the groups comprising two opposed coupling groups 245 serving as the coupling means engaging the coupling slots 233. Whereas thus only some of the spline elements serve as coupling means between the clutch element and the drive element they all serve as coupling means between the clutch element and the housing splines 204. In the shown embodiment the entire clutch element is manufactured in magnetic material, preferably moulded using a magnetic polymeric compound containing grinded magnetic particles, as this technique can produce intricate shapes. A large magnetic volume is subsequently obtained by magnetizing the whole part, thereby obtaining a larger external magnetic field with a larger magnetic moment than what would be possible with just a region of the part being magnetic. In the shown example a magnetic dipole oriented in the A-A direction is created. As will be described in greater detail below, the magnetic field can be detected by an electronic sensing component and the information be used to determine the rotational and/or axial position of the clutch element in relation to the sensor means, the clutch element thereby serving as an indicator element.

Figure 6:
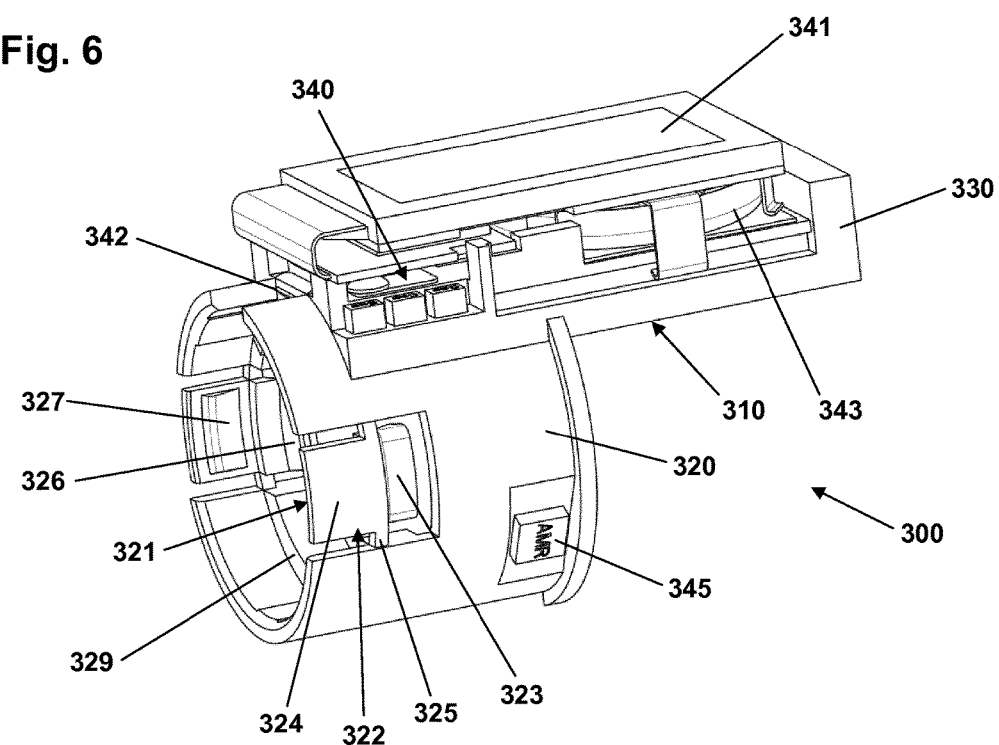
FIG. 6 shows components of a first embodiment of a logging module.

Turning to FIG. 6 an exemplary embodiment of a logging module 300 is shown in which the exterior housing has been removed to reveal the interior design and components. The module comprises a main body 310 having a generally cylindrical ring-formed portion 320 and a body portion 330 together forming a chassis on which the majority of the electronic circuitry is mounted. The main body is formed from a LDS polymer whereby integrated wiring can be achieved by using LDS (Laser Direct Structuring) technology, the polymer having elastic properties allowing a flexible hinged latch to be formed integrally. More specifically, the ring portion comprises an inner generally cylindrical surface adapted to be mounted on a drug delivery pen body as well as a pair of opposed integrally formed coupling structures 321 adapted to engage corresponding coupling structures on the pen device to assure that the module is securely mounted. The distal part of the ring portion has a larger diameter with a distally facing circumferential stop surface 329 adapted to receive and engage a cap when the module is mounted on a pen, see below.

The inner ring surface and the outer pen body surface may be in either form-fitting or slight frictional engagement. Each coupling structure on the module is in the form of a latch 322 having a proximal portion 323, a distal portion 324 and a central portion, the latter being pivotally connected to the ring portion by integrally formed flexible hinges 325 allowing the latch to pivot a few degrees corresponding to a circumferential axis. By this arrangement the distal latch portion moves inwards when the proximal portion is moved outwards and vice versa. The proximal latch portions each comprises an inner protrusion 326 adapted to engage a corresponding coupling structure on the pen device and the distal latch portions each comprises a protrusion 327 adapted to engage the cap when a cap is mounted on the pen body. To assure correct rotational mounting of the module on the pen the shown module is provided with a funnel-shaped slot 528 (see FIG. 8) adapted to axially engage a corresponding protrusion on the pen. In the shown embodiment of FIG. 1A the protrusion 212 is provided on the pen cartridge holder 210 and arranged opposite the pen display window 202, the electronic display 130 thereby being arranged next to the pen display window when the module is mounted on a pen. The interactions between the logging module, the pen body and the cap will be described in greater detail below.

On the body portion 330 the majority of the electronic components 340 including processor means, a display 341, a flexible cap switch 342 and a battery 343 are mounted. In the shown embodiment the logging module is provided with an exemplary sensor assembly comprising three "compass" sensor units 345 mounted equidistantly on the ring portion 320, each sensor unit being in the form of a magnetometer adapted to measure a magnetic field corresponding to three axes. The sensors as well as the majority of the electronic components being connected using LDS. Further sensors may be provided allowing e.g. the type of the device to be recognized. The logging module may be provided with user input means in the form of e.g. one or more buttons (not shown) allowing the user to control the module. The logging module may further be provided with transmission means allowing data to be transmitted to or from the module, e.g. log data may be transmitted to a user's smartphone by NFC or other wireless means.

Figure 7:
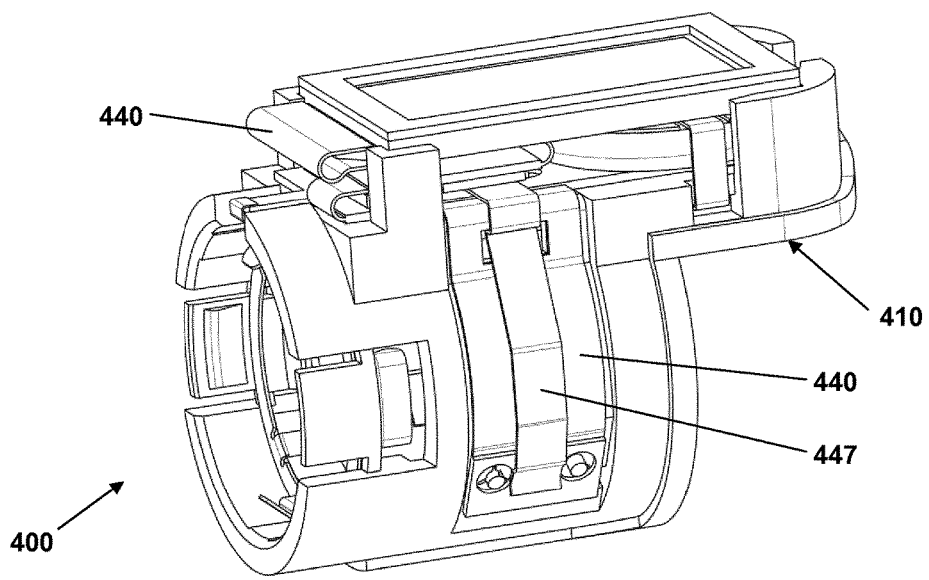
FIG. 7 shows components of a second embodiment of a logging module.

FIG. 7 shows an alternative embodiment 400 in which the electronics including the sensors are mounted on a flexible PCB 440 which then is mounted on the main body 410 using metal clips 447. As a further alternative a flexible PCB may be mounted by fully or partly bonding it to a chassis component using double-sided adhesive, this allowing an accurate, reliable and compact design.

In the embodiments of FIGS. 6 and 7 the LCD is of a traditional stiff type to be covered by a separate display window, however, alternatively a flexible LCD may be bonded directly to a transparent plastic cover providing a compact and robust design.

Figure 8:
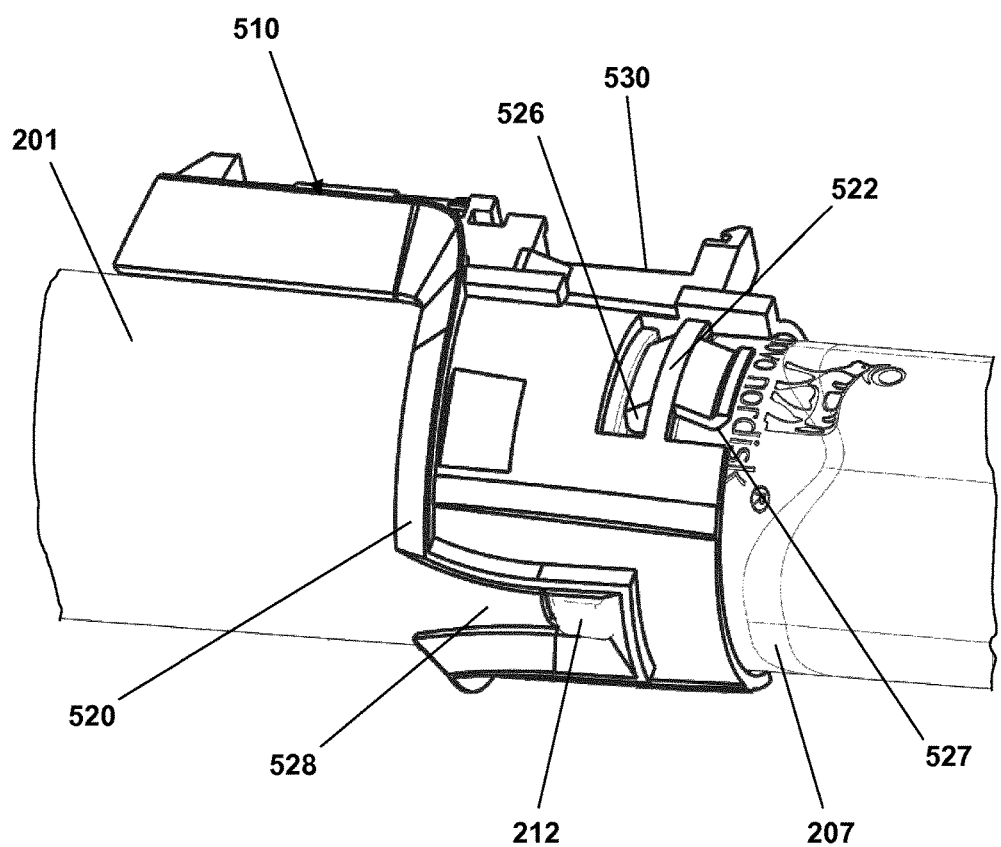
FIG. 8 shows a component of a third embodiment of a logging module mounted on a pen.

FIG. 8 shows an alternative embodiment of a module main body 510 comprising a generally cylindrical ring-formed portion 520 and a body portion 530, the main body being formed from a LDS polymer. Corresponding to the FIG. 6 embodiment the ring portion 520 is provided with a pair of opposed coupling latches 522 having proximal and distal coupling protrusions 526, 527 as well as a coupling slot 528.

Figure 9:
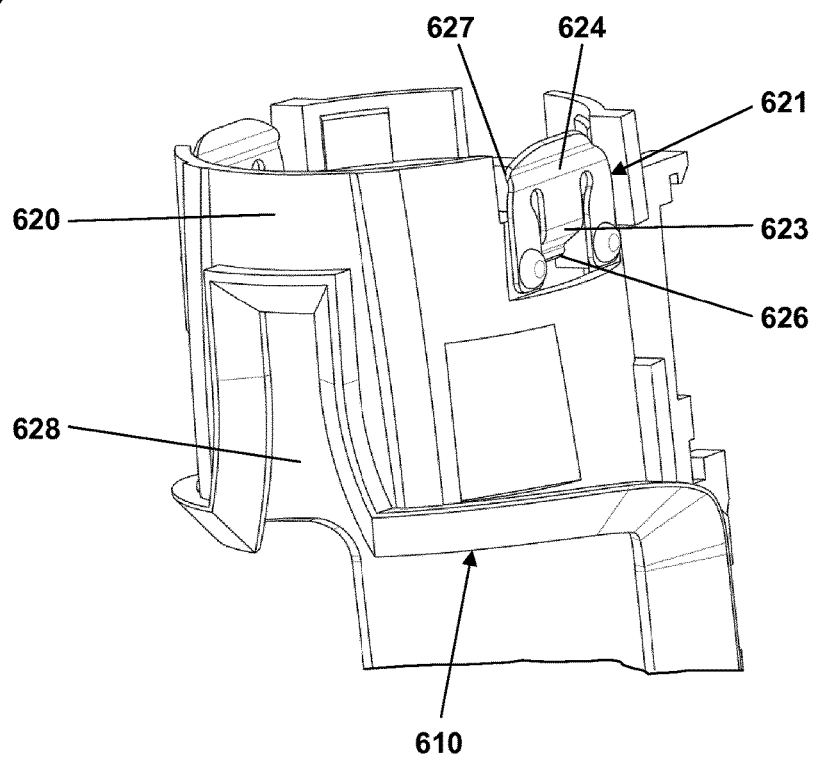
FIG. 9 shows a component of a fourth embodiment of a logging module.
Figure 10:
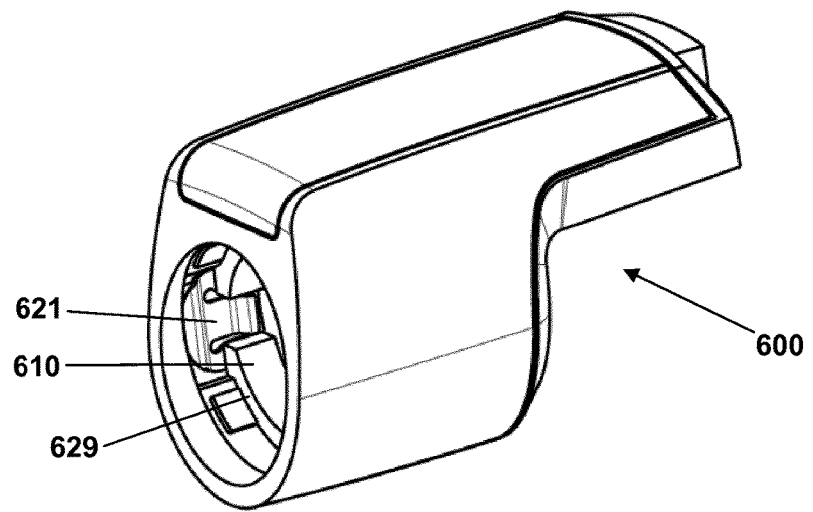
FIG. 10 shows an exterior view of the fourth embodiment of a logging module.

FIG. 9 shows a further alternative embodiment of a module main body 610 comprising a generally cylindrical ring-formed portion 620, however, in contrast to the above-described embodiments comprising integrally formed latches, the latch structures are here provided as separate metal latch members 621 attached to the ring portion. Corresponding to the integrally formed latches, each latch member comprises a proximal portion 623 with an inner protrusion 626 adapted to engage a corresponding coupling structure on the pen device, as well as a distal portion 624 with an inner protrusion 327 adapted to engage the cap when a cap is mounted on the pen body. In the shown embodiment the metal latch members each comprises a pair of proximal legs attached to the ring portion by rivets. The shown embodiment of a metal latch does not comprise a specific hinge structure, however, when mounted on a pen the latch member will provide the same "dual-purpose" functionality as the integrally formed latch, see below. FIG. 10 shows the main body 610 incorporated in a logging module 600 comprising a circumferential stop surface 629 and being provided with metal latch members 622.

With reference to FIGS. 2 and 8 mounting and operation of a logging module of the type shown in FIGS. 1A and 1B will be described. To mount the module on the pen body the cap is removed allowing the module to be slid over the cartridge holder 210. During mounting the user orients the module display 130 in line with the pen display 202 whereby the funnel-shaped slot 528 will catch the protrusion 212 which then will orient the module rotationally correct, this ensuring that the proximal latch protrusions 526 will snap into engagement with the cartridge protrusions 211, the module now being in its operational position, this allowing information to be transferred between the drug delivery device and the logging module (see below). As appears from FIG. 1B, in the mounted position a ring-formed gap 114 is formed between the cartridge holder and the distal portion of the module, this allowing the cap to be inserted into the gap as shown in FIGS. 1B and 8. For normal use without a mounted logging module the cap comprises inner coupling means adapted to engage the cartridge protrusions 211, however, with a mounted logging module the cartridge protrusions are "occupied". Correspondingly, the module is provided with the above-described distal latch protrusions 527 which in the shown embodiment frictionally engage the outer cap surface to securely hold it in place. In addition, also the flexible cap switch 342 contributes to hold the cap in place. Alternatively, the cap may be provided with coupling means, e.g. a circumferential groove, which would allow the cap to engage the module by snap action.

The coupling between the pen main part and the module is designed to provide both ease of attachment and a firm and secure grip during normal use, however, this should also be the case for the cap when attached to the pen in cooperation with the module. Correspondingly, when the cap is removed from the pen a distally directed force is transmitted to the coupling between the module and the pen via the coupling between the module and the cap which under given circumstances may result in the module being unintentionally pulled off the pen. To reduce the risk of this happening the module coupling latches 522 are provided with a "snap booster" feature. More specifically, each latch has a hinged design as described with reference to FIG. 6, this providing that the distal latch portion moves (further) inwards into the circumferential gap when the proximal latch portions are moved outwards as the module is mounted on the pen. As the proximal latch portions cannot be moved further inwards when the module is mounted, the outwards movement of the distal latch portions due to insertion of the cap into the gap 114 will result in an inwardly directed force being applied on the proximal latch portions via the latch central portion, this ensuring an enhanced grip between the module and the pen when the cap is mounted, this reducing the risk that the module is unintentionally pulled off the pen when the cap is removed. A proximal stop for the cap is provided by a circumferential stop surface of the module.

Having described the different components of the system, next a typical situation of use will be described with reference to FIGS. 1A and 1B. When the user desires to dispense a dose of drug, e.g. performing an intravenous injection of an amount of an insulin formulation, the cap 207 is removed and a needle assembly, if not already in place, is mounted on the cartridge holder coupling means 215. When the cap is removed the logging module is turned on from its sleeping state by activation of the module cap switch to its "on" position, e.g. the electronic circuitry with the sensor system is powered up and the display is turned on showing e.g. the last logged dose and the time since then. The user will then turn the rotatable dose member 280 to manually set a desired dose of drug shown in display window 202 and which can then be expelled when the button 290 is actuated. Depending on the design of the logging module a given dose may be registered corresponding to a set dose, an expelled dose or both. In the shown embodiment in which movement of the clutch element is detected it follows that only an expelled dose can be registered. Correspondingly, the module display will not show information in respect of the dose being set. When the dose has been set, the user releases the spring-driven expelling mechanism whereby the clutch element is released and starts to rotate in a fixed relationship to the expelled amount, this allowing the expelled amount to be determined by the logging module. As the module has not acquired information in respect of the set dose and as the expelling of a set dose can be paused by releasing the pressure on the release button, a given dose, e.g. a large dose, may be split into two or more amounts, which would result in the logging of two or more expelled doses. Correspondingly, to treat such split doses as a single dose the shown logging module is designed to combine and log individual doses as a single dose under given circumstances, typically within a given window of time, e.g. 5 seconds, after which the "combine feature" would time out. For an extended window of e.g. 5 minutes such a feature would also allow the module to be moved to a new pen should a given desired dose be larger than the amount of drug remaining in the cartridge of a used pen. If it for any reason is desired to have split doses logged individually the "combine window" can be closed by mounting the cap on the pen to thereby bring the cap switch in its "off" position terminating a logging event. Correspondingly, during normal operation in which a given dose is expelled as a single amount of drug the combine window is closed when the cap is mounted, this resulting in the determined dose (single or combined) being logged in the memory together with a time value as well as displayed in the electronic display for a given amount of time, e.g. 30 seconds, before the electronics power down and the display is turned off.

Turning to the sensor system of the logging module, the shown embodiment may be designed to detect one or more movements of one or more magnetic members. For example, a "simple" design may be implemented in which the number of incremental rotational movements of the clutch element is counted, i.e. the number of 15 degrees increments, each increment corresponding to 1 unit (IU) of insulin. The system would be designed to scan the pen at a frequency sufficiently high to securely detect that the clutch element has moved into a new of 24 pre-determined sectors each corresponding to 15 degrees rotation and thus 1 IU. Using the same basic sensor design and sensor positions a magnetic drive element could be used as an alternative magnetic element. As a further alternative using the same general sensor design a component which is moved in accordance with both the set and the expelled dose could be used as a magnetic element, e.g. the ratchet tube. As the ratchet tube extends axially outside the part of the pen enclosed by the module ring only a portion of the ratchet tube may have magnetic properties, e.g. provided by a separate element.

As a yet further alternative the sensor system may be designed to determine the absolute rotational position of a given element, however, as most pens using a rotating expelling mechanism are designed to expel a dose size requiring more than one full rotation of a given element, it would be necessary to count the number of full revolution. This could be accomplished using the same magnetic element to both count incremental movement (here: number of rotations) and an absolute position. The same or different sensor systems may be provided to detect the two type of information. Determination of an absolute position would prevent errors due to missed counts. Alternatively the sensor system may be designed to use an additional "secondary" element which is moved axially as a dose is expelled to indicate full rotations of the "primary" rotating element, e.g. a magnetic EOC member, however, as the movement of such an element primarily takes place outside the part of the pen enclosed by the module ring it may be necessary to provide further sensors.

In the following an exemplary magnetometer-based detection system will be described which basically can accurately detect the position of a magnet moving in a predefined way, e.g. rotating relative to an axis. The system is therefore applicable in many technical areas in which accurate non-contact position sensing is relevant. In the following a system will be described which has been set up for application in a drug delivery system comprising a magnetic member which is configured to perform a rotational as well as axial movement, see e.g. FIG. 4A, and which will determine the absolute rotational position of a magnetic member.

In FIG. 6 an exemplary embodiment of a sensor assembly is configured as comprising three 3D magnetic "compass" sensors 345 equidistantly around the pre-determined axis for the above-described ring-formed clutch element rotating inside the distal portion of a pen-formed drug delivery.

In the following an exemplary "position" algorithm for estimating a current orientation of a magnet will be described. The algorithm is general to any movement of a magnet, but in the present application, it is applied to a system with rotational movement of a magnet.

The algorithm is adapted for a system having deviations from nominal movement of the magnet. Therefore, it requires a pre-determined model of the magnet movement from which one can derive derivatives. Let $B_{nom}^k(n)$ denote the field having nominal geometry of the system, where n is the position of the axial displacement and k is the sensor measuring the field.

If the magnet has a given geometry and if the relative distance between sensors and magnet is assumed to be in the magnetic far-field for all positions, the pre-determined model can be estimated using a dipole field model. Thus, we can estimate $B_{nom}^k(n)$ to all positions by the following:

$$B_{nom}^k(n) = \frac{1}{4\pi}\left[\frac{3(m \cdot r)}{r^5} - \frac{m}{r^3}\right] \quad [1]$$

Where m is the dipole moment vector of that given position n, r is the distance vector between the magnet and the sensor k and r is the distance between the magnet and sensor k.

If the sensors are positioned in the magnetic near-field, then $B_{nom}^k(n)$ can be estimated using Finite Element analysis of the magnet geometry.

The concept is to have a model that both estimates the non-nominal behaviour and compensates the pre-determined nominal model, if non-nominal behaviour is found to be acceptable. In order to do so, a linearized model of the pre-determined model is defined:

$$\hat{B}_{k,n}(B^{ext}, \Delta x, \Delta y, \Delta z, \Delta m, \Delta\varphi, \Delta\psi) = \quad [2]$$

$$B_{nom}^k(n) + B^{ext} + \left[\frac{\partial B}{\partial x}\right]_{k,n}^{nom} \Delta x + \left[\frac{\partial B}{\partial y}\right]_{k,n}^{nom} \Delta y + \ldots + \left[\frac{\partial B}{\partial \psi}\right]_{k,n}^{nom} \Delta\psi$$

Where the following Deviation parameters have been included in the linearized model:

| | |
|---|---|
| $B^{ext}$ | Uniform background field |
| $\Delta x, \Delta y$ | Radial offsets of magnet position relative to nominal model |
| $\Delta z$ | Axial offset of magnet position relative to nominal model |
| $\Delta m$ | Deviation from nominal magnet strength |
| $\Delta\varphi$ | Rotational offset |
| $\Delta\psi$ | Tilt offset |

Stacking the Deviation parameters in a column vector E:

$$E = \begin{bmatrix} B_6^{ext} \\ B_y^{ext} \\ B_z^{ext} \\ \Delta x \\ \Delta y \\ \Delta z \\ \Delta m \\ \Delta\varphi \\ \Delta\psi \end{bmatrix} \quad [3]$$

We can write a linearized model as:

$$\hat{b}_n(E) = b_n^{nom} + J_n E \quad [4]$$

Where $J_n = \partial b_n^{nom}/\partial E$ is the Jacobian matrix. Then we determine E to minimize the difference between the measured field and the linearized model. I.e.:

$$\frac{\partial \|b^{meas} - \hat{b}_n(E)\|}{\partial E} = 2J_n^T G_n(b_n^{nom} + J_n E - b^{meas}) = 0 \quad [5]$$

Where $G_n$ denotes a diagonal matrix with weights for each sensor k and position n. Thus, E is given by:

$$E_n^{min} J_n^T G_n J_n]^{-1}[J_n^T G_n(b^{meas} - b_n^{nom})] \quad [6]$$

The above expression can be simplified to the following:

$$E_n^{min} = M_n(b^{meas} - b_n^{nom}) \quad [7]$$

Where:

$$M_n J_n^T G_n J_n]^{-1}[J_n^T G_n] \quad [8]$$

This matrix is constant. Thus, it can be stored on the processor to save computational power.

The parameter offset vector, $E_n^{min}$, is then inserted into the linearized model:

$$\hat{b}_n(E_n^{min}) = b_n^{nom} + J_n E_n^{min} \quad [9]$$

This provides an updated version of the nominal model accounting for the difference between the measured field and the nominal model. The estimated position is found to be the position with the smallest difference, i.e. minimizing the residual:

$$r_n = \|b^{meas} - \hat{b}_n(E_n^{min})\| \quad [10]$$

The advantages of the above algorithm are:

The algorithm makes use of constant tables that can be stored on the processor, i.e. it consists of $b_n^{nom}$, $J_n$ and $M_n$. The algorithm provides measures that can be used as fail-safe measure, i.e. the quality of the fit can be estimated from $E_n^{min}$ and the size of the residuals, $r_n$. The shown column vector E is merely an example of selected deviation parameters.

Using the same principles as described above, the axial z-position of a given member could be determined, e.g. the clutch member.

In the following a "tracking" algorithm for determining the number of full clutch rotations will be described based on the same principles as the position algorithm, but having been optimised for calculation speed and power consumption. The position algorithm uses the input from all available magnetic sensors, whereas the tracking algorithm may be based on e.g. 2-4 axes from one or more of the three-axis magnetic sensors. In other words, the sensor system assembly is operated to provide first as well as second sensor means providing input for the position respectively the tracking algorithm. In the following, the three axes from one sensor are used. The Tracking algorithm takes the measured field as input, $B_{meas}$ and the most recently estimated background field from the position algorithm, $B_{ext}$. The residual difference between a measured B-field and nominal B-field, $B_{nom}$, is derived as:

$$r(n) = [B_{meas} - B_{ext} - B_{nom}(n)]^2 \quad [11]$$

Where n denotes the number of tables positions. In the examples, 48 positions are included in $B_{nom}$, the field for 24 clutch positions in dose setting and 24 positions in dosing position. Based on the lowest residual, the tracking algorithm outputs a binary axial position, z=[dose setting; dosing] and a discrete rotational position, phi=[0 15 30 . . . 345]°.

The tracking algorithm will have less accuracy than the position algorithm, e.g. ±30°, but due to lower power consumption, it can be sampled more often. The sampling frequency should be adjusted to the minimum rotation time of the clutch. For example, if the minimum rotation time of the clutch is 500 ms and it is desired to have a least 10 tracking samples for each rotation, then the sampling rate of the tracking algorithm should be at least 20 Hz. In this way, the tracking algorithm will be able to count the number of revolutions of the clutch in-between the estimates by the position algorithm, which is sampled at a lower frequency to save power.

If the risk of external magnetic fields other than earth's magnetic field and disturbances in the internal magnetic field by the presence of iron nearby can be positively excluded, the most likely candidate of actual position found in the table can be relayed or displayed as actual position. However, in most applications the risk of disturbances in the magnetic field must be considered likely from a variety of sources and in some applications the consequences of a wrong determination of position could have serious and unacceptable consequences. In such applications a number of fail-safe measures can be taken, for example:

(1) Taking a number of readings and use mean axis value from each axis from each sensor only when variations between readings are less than a predefined level. This could prevent wrong readings from the sensors caused by a fluctuating disturbance in the magnetic field.

(2) Subtracting readings from diametrically opposite sensors to eliminate the magnet field contribution and the homogenous external field contribution and hence calculate the gradient of an inhomogeneous external field. Comparison against threshold values may be used as criteria for using the readings.

(3) Using readings to calculate the external field. Comparison against threshold values may be used as criteria for using the readings.

(4) Using readings from an over-determined sensor configuration to calculate deviations from pre-determined nominal mechanical geometry and magnet characteristics. Comparison against threshold values may be used as criteria for using the readings.

(5) Comparing the deviance of the most likely position and the deviances of rejected positions (e.g. the second most likely position) to determine the credibility of the most likely position. Comparison against threshold values may be used as criteria for using the readings.

(6) Comparing the most likely position and rejected positions, e.g. the top 10 next most likely positions, to determine the distribution of the positions. The distribution, e.g. span between minimum and maximum position, may be used as criteria for using the readings.

(7) Using the most likely position to calculate the field contribution from the magnet and subtracting the contribution from the readings to obtain an estimated external field. The estimated external field may be used as input for calculating a most likely position which should be rejected by one or more of the fail-safe measures since the field contribution from the magnet has been eliminated. The field contribution from a position different from the most likely positions may be calculated and added to the estimated external field. The resulting field may be used as input for calculating a most likely position. Correspondence between the selected position and calculated position may be used as criteria for using the readings.

(8) Using calculated positions to determine the mechanical movement, e.g. direction, speed and position stability. Comparison against threshold values may be used as criteria for using the readings.

(9) Only appoint a most likely candidate of actual position if the minimum sum of deviance is less than a predefined value, to ensure a certain level of coherence between measured values and (expected) table values. This predefined value may be dependent on where in the range of operation the most likely candidate is, since the distances between neighboring candidates vary with distance from sensor. This should prevent a constant disturbance above a certain magnitude from causing the wrong position to be appointed most likely candidate and can also prevent a most likely candidate from being appointed if one of the sensors axis' have gone into saturated mode. If sensors are exposed to a magnetic field of a strength exceeding their limit of operation, they will go into saturation mode and give a readout of (a known predefined) maximum value.

The above mentioned fail-safe measures will only be able to help prevent read-out of dose data based on false positions by giving no read-out at all. The system can then (if change of position is either prevented or monitored not to occur) repeat measurements until the system is clear of the external disturbance of the internal magnetic field.

Summarizing the above, when we consider the movement pattern of the clutch element a dosing event will be a forward axial movement, a rotational movement corresponding to the number of units dialed and a backwards axial movement, when the dose button is released. In this case, the rotational positions will be repeated for each 24 increments. As appears, a measurement before and after a movement event cannot be used to determine the total change in increments and therefore it is required to monitor the clutch while it is moving. In order to ensure that all revolutions are counted, it is required that the sampling frequency is high which potentially may give rise to a high power consumption. If the sampling frequency is too low not all revolutions may be counted and the system may potentially display a wrong dose to the user, e.g. 1 IU when 25 IU is dialed and expelled.

Figure 11:
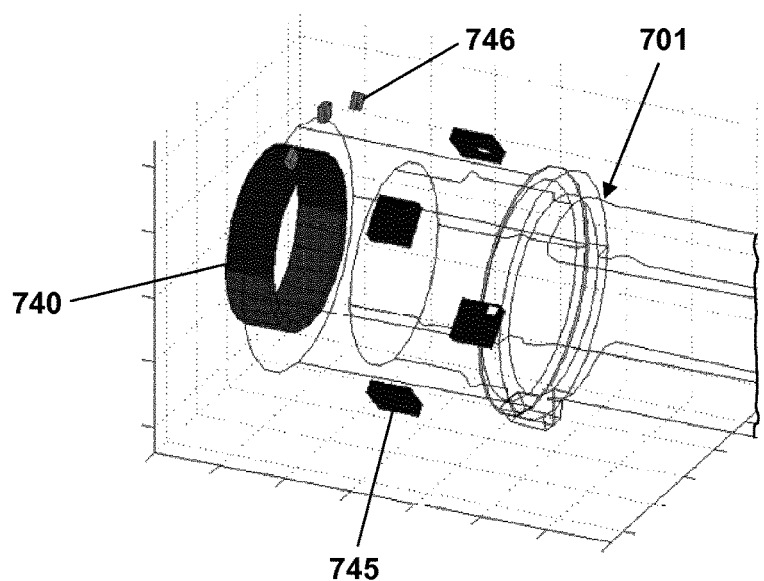
FIG. 11 shows schematically a sensor system.

The practical solution to this issue would be to keep track of the number of revolutions while having reasonable power consumption. Correspondingly, in a second exemplary embodiment of a sensor system this issue is addressed by having three algorithms based on two sensor systems. In the following the three algorithms are named position algorithm, tracking algorithm and high-speed algorithm. As shown schematically in FIG. 11 the sensor system is comprised by four three-axis magnetic compass sensors 745 and two or three "giant magneto-resistive" (GMR) sensors 746, the figure showing the sensor positions relative to the drug delivery device 701 and the clutch ring 740.

The Position algorithm estimates the rotational and axial position of the clutch and the homogenous component of the background field and generally corresponds to the above-described algorithm.

The Tracking algorithm is based on the same principles as the position algorithm, but it has been optimised for calculation speed and power consumption. The position algorithm uses the input from all four magnetic sensors, whereas the tracking algorithm is based on 2-4 axes from one or more three-axis magnetic sensors. In the following exemplary embodiment the three axes from one sensor are used. The Tracking algorithm takes the measured field as input, $B_{meas}$ and the most recently estimated background field from the position algorithm, $B_{ext}$. The residual difference between a measured B-field and nominal B-field, $B_{nom}$, is derived as (see above):

$$r(n)=[B_{meas}-B_{ext}-B_{nom}(n)]^2 \qquad [11]$$

Where n denotes the number of tables positions. In the examples, 48 positions are included in $B_{nom}$, the field for 24 clutch positions in dose setting and 24 positions in dosing position. Based on the lowest residual, the tracking algorithm outputs a binary axial position, z=[Dose Setting; Dosing] and a discrete rotational position, phi=[0 15 30 . . . 345]°.

Figure 12:
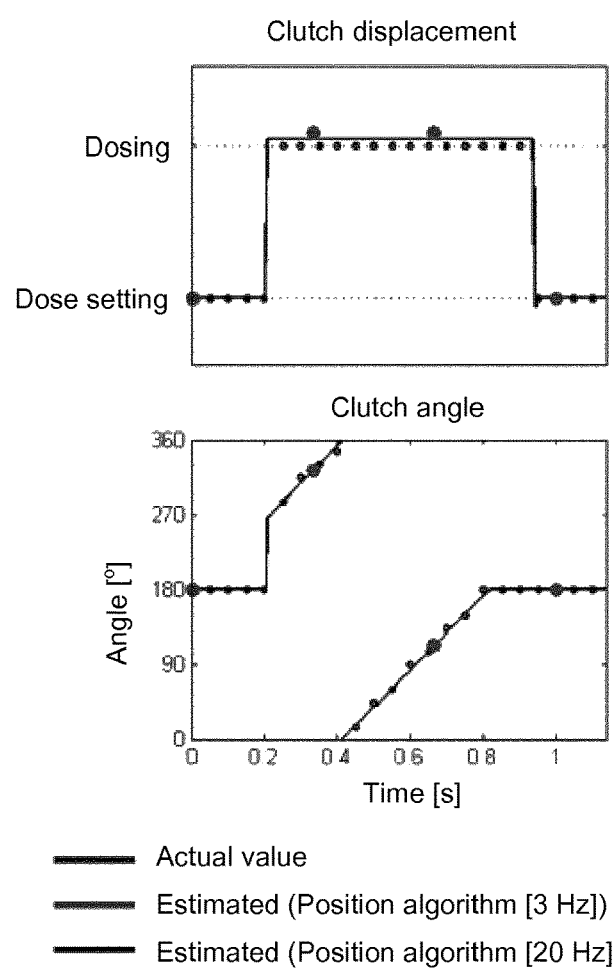
FIG. 12 shows for the sensor system of FIG. 11 algorithm output for a dosing event.

The tracking algorithm will have less accuracy than the position algorithm, e.g. ±30°, but due to lower power consumption, it can be sampled more often. The sampling frequency should be adjusted to the minimum rotation time of the clutch. For example, if the minimum rotation time of the clutch is 500 ms and it is decided to have a least 10 tracking samples for each rotation, then the sampling rate of the tracking algorithm should be at least 20 Hz. In this way, the tracking algorithm will be able to count the number of revolutions of the clutch in-between the estimates by the position algorithm, which is sampled at a lower frequency to save power. Output from the position and tracking algorithms for a dosing event is shown in FIG. 12

Sampling at 20 Hz implies that a rotation can be missed if the rotation time is shorter than approximately 50 ms (~40 ms taking the lower accuracy into account). Such a situation could be the case if there is a large air gap between the piston rod and the cartridge piston, e.g. more than 16 IU, where the rotation time for a give system could be as low as 6-7 ms. The power consumption makes it unfeasible to increase the sampling frequency of the tracking algorithm to count revolutions in this case. Addressing this issue, GMR sensors and a high-speed algorithm is utilized.

In a first exemplary embodiment the high-speed algorithm takes the value from three GMR sensors as input. The sensor output is binary (e.g. 1 if the field in the sensor component is greater than ±threshold and 0 if in the range from −threshold to +threshold, where the threshold could be e.g. 12 Gauss). GMR sensors cannot distinguish between a positive and a negative magnetic field. A GMR sensor has a magnetic switch that turns on when the magnetic field is applied and turns off when the field is removed. The power consumption is almost negligible when the switch is unchanged. A transition from 0→1 or 1→0 is counted by the high-speed algorithm. Ideally, each GMR sensor returns four transitions for each rotation of the clutch, i.e. 12 transitions for each rotation can be expected. At very fast rotational speed, the transitions will come within a short time period. In the exemplary embodiment the high-speed algorithm detects high-speed if 9 or more transitions are observed within a continuous time frame of 15 ms with at least 3 transitions per GMR sensor which would enable the system to detect rotation times of up to 20 ms. At smaller air gaps, the rotation time is significant larger due to system being slowed down by the cartridge piston.

The reason that it is acceptable for some transitions to be omitted is that it is possible to mask one or two transitions with an external magnet or due to tolerances in the system. The reason for the relatively short time window is to reduce the number of false detections by mechanical tolerances, user activities and external magnets. In addition, the GMR sensors should have some hysteresis in order to reduce noise. The hysteresis implies that a transition from 0→1 at e.g. 12 Gauss is followed by a transition from 1→0 if only the field comes below 10 e.g. Gauss. In this way, noise is reduced if the field is changing around the threshold. In the exemplary embodiment the three GMR sensors are distributed angularly around the clutch. Ideally, they should be positioned with 45 degree separation, to get the largest difference in field, e.g. sensor 1 being orthogonal to sensor 3. In addition, a homogeneous background field will have a smaller impact on all three sensors if they observe the field in different directions.

In a second exemplary embodiment the high-speed algorithm takes the value from two GMR sensors as input supplemented with a further criteria such that a high-speed condition is detected when 8 or more transitions are observed within a continuous time frame of 15 ms with at least 3 transitions per sensor or 6-7 transitions are counted within 15 ms and a change in phi-Position within +/−60 degrees and the clutch is moving forward to dosing position (z-position).

The algorithms are integrated in the following way:
1. The output from the tracking algorithm is accumulated→phiTrackAccum
2. The 5 consecutive outputs from the position algorithm are processed and the stability and reliability of the angles are assessed by several parameters, e.g. based on goodness of fit, external interference and movement in system (see example below). If the criteria for a stable and reliable angle are fulfilled for all 5 of the consecutive outputs, then the clutch angle is taken as a mean of the five angle estimates→phiStable.
3. Each time a stable angle is derived, it is checked whether the clutch has moved. The criterion for movement is either that phiTrackAccum (or phiTA) has increased more than e.g. 180 degree or phiStable has changed more than e.g. 7.5 degree. phiStable is calculated continuously until clutch movement has been detected.
4. If movement has been detected, then the dose size can be derived by the following:

Example 1

The input for the movement criteria are the following:
phiStable(start)=30°
phiStable(end)=210°
phiTA=195°
ΔphiStable=180°
The number of revolutions is estimated by:
phiRemainder=phiTA−ΔphiStable
phiRemainder=195°−180°
phiRemainder=15°
N=round(phiRemainder/360°)
N=round(0.04)
N=0
Dose size in degree:
doseSizePhi=ΔphiStable+N*360°
doseSizePhi=180°+0*360°=180°
Dose size in IU:
doseSizeIU=round(doseSizePhi/15°)
doseSizeIU=round(180°/15°)
doseSizeIU=12 IU Example 2

The input for the movement criteria are the following:
phiStable(start)=15°
phiStable(end)=45°
phiTA=405°
ΔphiStable=30°
The number of revolutions is estimated by:
phiRemainder=phiTA−ΔphiStable
phiRemainder=405°−30°
phiRemainder=375°
N=round(phiRemainder/360°)
N=round(1.04)
N=1
Dose size in degree:
doseSizePhi=ΔphiStable+N*360°
doseSizePhi=30°+1*360°=390°
Dose size in IU:
doseSizeIU=round(doseSizePhi/15°)
doseSizeIU=round(390°/15°)
doseSizeIU=26 IU
phiTA is reset after a dose size has been calculated.
If the high-speed algorithm is triggered, no dose size will be reported to the user.

To meet the overall criteria of a stable angle estimate one or more of the following criteria may be implemented.

Criterion 1: z-position. This criterion is related to the goodness of fit to the nominal model. The nominal model is specified for a clutch position in the dose setting position. The position algorithm becomes more sensitive to deviations when the estimated z-position deviates from the nominal position. In addition, the clutch is not fixates by the teeth in the housing and it is likely to be more tilted or radially displaced.

Criterion 2: Range of phiPosition. This criterion is related to movement of clutch and external interference. If the pen is dosing the angle estimate will change across the nSamplesobservations. In presence of inhomogeneous B-field, the phiPosition could also vary from sample to sample.

Criterion 3: Residual value. This criterion is related to goodness of fit and external interference. The residual value is highly correlated to the goodness of model-fit. Thus, the residual value contains all other deviations that cannot be explained by the compensation factors of the position algorithm, i.e. phi-position offset, z-position offset, and homogeneous component of the external B-field. In addition, the residual is correlated with presence of inhomogeneous B-field.

Criterion 4: Range of z-position. This criterion is related to external interference and movement in system. Obviously, the criterion is highly related to dose button activity. In presence of inhomogeneous B-field, the z-position could also vary from sample to sample.

Criterion 5: External B-field. This criterion is related to external interference. The criterion takes the estimated homogeneous B-field as input, Bext. Normally, the magnitude is in the range of 0.5±0.3 Gauss. The inhomogeneous part of an external field is usually proportional to the magnitude of the homogenous part. The size of the estimated homogeneous B-field can therefore be used as an indirect measure of external interference.

Criterion 6: Range of external B-field. This criterion is related to external interference. The criterion takes Bext as input. If the magnitude of Bext varies too much across the nSamplesobservations, then this criterion fails.

Criterion 7: Inconsistency between Tracking and Position. This criterion is related to movement in the system and external interference. The criterion compares if the angles estimated by the Tracking algorithm and the Position algorithm deviates too much. If that is the case, the clutch might be rotating or system might be exposed to external interference.

In addition to the above-described high-speed condition one or more of the following additional dose acceptance criteria may be used:

Residual value of position algorithm: If the residual value of the Position value exceeds a specified threshold the measurement is not reliable and the criterion fails.

External B-field: The criterion takes the estimated homogeneous B-field as input, Bext. If the specified threshold is exceeded the measurement is not reliable.

phiTA change rate: This criterion fails if phiTA has accumulated more than 360° across two observations. This criterion would target transient noise causing phiTrack to flip back and forth between two positions.

When providing a system having multiple algorithms consistency and redundancy can be checked in-between the algorithms and various safety and reliability measures can be applied to the described algorithms. For example, if the tracking algorithm and the position algorithm do not agree on the start and end angles of the clutch, the derived dose size could be disqualified. In addition, transitions from the GMR sensors during normal rotation speed could be used to verify consistency between the GMR sensor input and the tracking algorithm.

Figure 13:
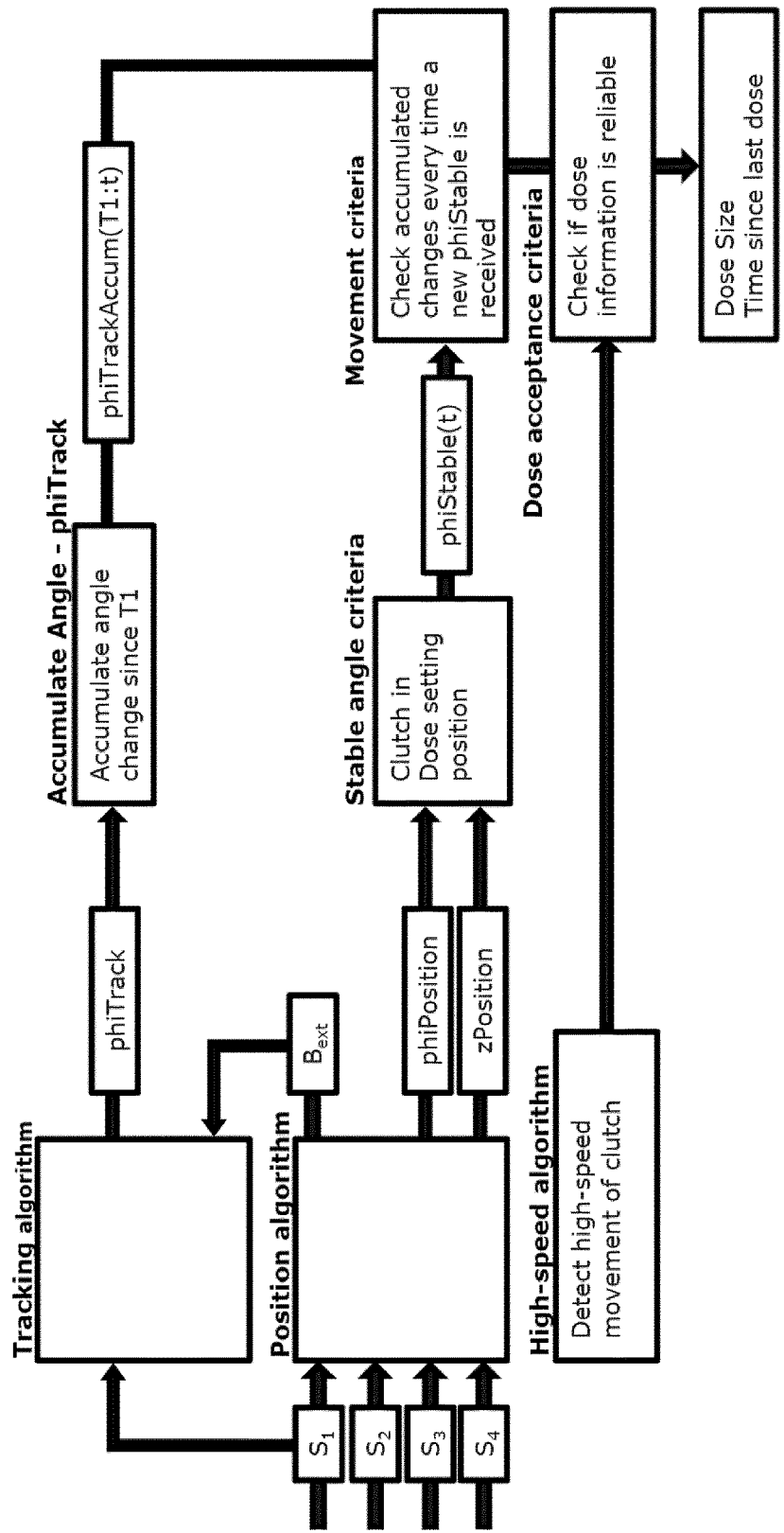
FIG. 13 shows a flowchart illustrating algorithm integration for the sensor system of FIG. 11.

FIG. 13 summarizes algorithm integration for the above-described exemplary sensor system.

In the above second exemplary embodiment of a sensor system a high-speed algorithm is used in combination with a position algorithm and a tracking algorithm, however, in alternative embodiments the high-speed algorithm may be used in combination with only a single detection algorithm, e.g. a position algorithm in case the indicator element is adapted to rotate less than 360 degrees, or an incremental counting algorithm as described above.

As a given pre-filled drug delivery device may be part of a system it may be provided to the users with different types of drugs, e.g. drugs for the treatment of different conditions such as diabetes and growth disorders, different classes of drugs for the treatment of a given condition such as insulins and GLP-1 for treatment of diabetes, different types of drugs from a given class such as long-acting and fast-acting insulin formulations, or different concentrations for a given specific drug such as 100 IU or 200 IU of insulin per ml of formulation. Although the above-described logging module normally would be designed to be mounted on only one type of drug delivery device it could in theory be mounted on devises containing a variety of different drugs.

To prevent that a given logging module would be used in a way resulting in incorrect determination of dose data, it should be ensured that a given logging module in a given state is used in combination with the corresponding drug.

For example, a given logging module may be adapted to be used with only one type of drug, e.g. a given insulin formulation having a given concentration, this being indicated on the logging module e.g. by text, colour or other visual markings. Indeed, this would still allow a given logging module to be used in combination with the wrong delivery device. To prevent this from taking place the logging module and the different delivery devices of a given system may be coded allowing mating of only modules and devices corresponding to each other, for example mechanically, magnetically (e.g. different magnetic strengths of the clutch member) or electronically.

For example, when a given pen type is used for different types of drugs it will be marked accordingly, e.g. by text, colour and/or codes. By providing such visual markings on the pen body on the part of the surface which would be covered by a mounted logging module, the logging module could be provided with optical sensor means adapted to detect such markings. For example, a given pen device may be fully or partly manufactured from a material having a given colour or it may be provided with a label having a given colour.

If a given logging module is adapted to be used only for one type of drug it would require that the corresponding colour is positively identified, otherwise the logging module would indicate an error condition. Alternatively, the logging module may be adapted to be used in combination with a variety of drugs, such that the positive identification of a given pre-specified colour would set up the logging module accordingly. For example, when mounted on a pen device with insulin of a given concentration it would register and display the correct number of IU, whereas when mounted on a pen device with GLP-1 of a given concentration it would register and display the correct number of mg. The type or brand name of the drug may be displayed e.g. a short time each time the display is turned on.

In the above description of exemplary embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A drug delivery system, comprising:
a drug-filled cartridge or structure for receiving a drug-filled cartridge, the cartridge comprising an outlet and an axially displaceable piston,
a first sensor structure comprising one or more sensors each adapted to measure a magnetic field corresponding to at least two axes,
a second sensor structure comprising one or more sensors each adapted to measure a magnetic field corresponding to at least one axis,
an expelling assembly for expelling an amount of drug from the drug filled cartridge, comprising:
a setting structure allowing a user to set a dose amount of drug to be expelled,
an actuation structure for releasing or driving the drug expelling assembly to expel the set dose amount, and
an indicator element adapted to rotate during expelling of an amount of drug, the indicator element comprising a magnet moving together therewith, the magnet being configured to generate a spatial magnetic field which relative to the sensor(s) of the first and/or second sensor structure varies corresponding to the spatial orientation of the magnet and thus the indicator element, thereby generating a spatial magnetic field which varies relative to each of the first and/or second sensor(s) as the indicator element moves,
processor structure configured to:
on the basis of measured values from the first sensor structure, determine a rotational position of the indicator element,
calculate an expelled dose amount based on determined rotational positions of the first indicator structure,
on the basis of measured values from the second sensor structure, determine a high-speed condition in which the rotational speed of the indicator element exceeds a given threshold level, and
indicate an error state if the high-speed condition is detected.

2. A drug delivery system as in claim 1, further comprising:
third sensor structure comprising one or more sensors each adapted to measure a magnetic field corresponding to at least one axis,
wherein the processor structure is configured to determine on the basis of measured values from a third sensor structure the number of full rotations of the indicator element.

3. A drug delivery system as in claim 2, comprising:
a first sensor assembly comprising two or more sensors adapted to measure a magnetic field corresponding to a plurality of axes,
wherein the first sensor structure is provided by the first sensor assembly operated to measure a magnetic field corresponding to a first number of axes, and the third sensor structure is provided by the first sensor assembly operated to measure a magnetic field corresponding to a second lower number of axes.

4. A drug delivery system as in claim 3, wherein:
the sensor(s) of the first sensor structure has/have a first sampling frequency, and
the sensor(s) of the third sensor structure has/have a second higher sampling frequency.

5. A drug delivery system as in claim 1, wherein:
the second sensor structure is provided by a second sensor assembly comprising two or more sensors.

6. A drug delivery system as in claim 5, wherein the sensor(s) of the second sensor assembly is/are adapted to detect a magnetic change-of-state.

7. A drug delivery system as in claim 1, wherein:
the indicator element rotates during expelling of drug, and
the processor structure and sensor structure form part of an electronically controlled capturing system for capturing data representing a property related to the amount of drug expelled from a reservoir by the expelling assembly during expelling of a set dose, the property being rotational movement of the indicator element.

8. A drug delivery system as defined in claim 1, wherein the indicator element is formed fully or partly of a polymeric material containing magnetic particles, the polymeric material having been magnetized to provide a magnet producing the magnetic spatial field, and wherein the indicator element may be ring-formed.

9. A drug delivery system as defined in claim 1, the system being in the form of an assembly comprising a drug delivery device and a logging device adapted to be releasably attached to the drug delivery device, wherein:
the drug delivery device comprises the expelling assembly, and
the logging device comprises the first sensor structure, the second sensor structure, and the processor structure.

10. A logging device adapted to be releasably attached to a drug delivery device, the drug delivery device comprising:
a drug reservoir or structure for receiving a drug reservoir,
drug expelling structure comprising dose setting structure allowing a user to set a dose amount of drug to be expelled, and
an indicator element comprising a magnet moving together therewith, the magnet being configured to generate a spatial magnetic field which relative to external sensor structure varies corresponding to the rotational orientation of the magnet and thus the indicator element, wherein the indicator element is adapted to rotate during operation of the expelling structure corresponding to an axis of rotation, the amount of rotation corresponding to the amount of drug expelled from a reservoir by the drug expelling structure,
the logging device comprising:
a first sensor structure comprising one or more sensors each adapted to measure a magnetic field corresponding to at least two axes,
a second sensor structure comprising one or more sensors each adapted to measure a magnetic field corresponding to at least one axis,
a storage structure adapted to store one or more dose amounts to create a log, and
a processor structure configured to determine:
on the basis of measured values from the first sensor structure, a rotational position of the indicator element,
on the basis of measured values from the second sensor structure, a high-speed condition in which the rotational speed of the indicator element exceeds a given threshold level, and
indicate an error state if the high-speed condition is detected.

11. A logging device as in claim 10, further comprising:
a third sensor structure comprising one or more sensors each adapted to measure a magnetic field corresponding to at least one axis,
wherein the processor structure is configured to determine on the basis of measured values from the third sensor structure the number of full rotations of the indicator element.

12. A logging device as in claim 11, comprising:
a first sensor assembly comprising two or more sensors adapted to measure a magnetic field corresponding to a plurality of axes,
wherein the first sensor structure is provided by the sensor assembly operated to measure a magnetic field corresponding to a first number of axes, and the third sensor structure is provided by the sensor assembly operated to measure a magnetic field corresponding to a second lower number of axes.

13. A logging device as in claim 12, wherein:
the sensor(s) of the first sensor structure has/have a first sampling frequency, and
the sensor(s) of the third sensor structure has/have a second higher sampling frequency.

14. A logging device as in claim 10, wherein:
the second sensor structure is provided by a second sensor assembly comprising one or more further sensors.

15. A drug delivery system as in claim 14, wherein the sensor(s) of the second sensor assembly is/are adapted to detect a magnetic change-of-state.

* * * * *

UNITED STATES PATENT AND TRADEMARK OFFICE
CERTIFICATE OF CORRECTION

PATENT NO. : 10,384,013 B2
APPLICATION NO. : 15/515188
DATED : August 20, 2019
INVENTOR(S) : Krusell et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 159 days.

Signed and Sealed this
Second Day of June, 2020

Andrei Iancu
*Director of the United States Patent and Trademark Office*